(12) United States Patent
Moine et al.

(10) Patent No.: US 11,597,936 B2
(45) Date of Patent: Mar. 7, 2023

(54) RECOMBINANT DGKK GENE FOR FRAGILE X SYNDROME GENE THERAPY

(71) Applicants: UNIVERSITE DE STRASBOURG, Strasbourg (FR); CENTRE NATIONAL DE LA RECHERCHE SCIENTIFIQUE, Paris (FR); INSTITUT NATIONAL DE LA SANTE ET DE LA RECHERCHE MEDICALE, Paris (FR)

(72) Inventors: Hervé Moine, Strasbourg (FR); Ricardos Tabet, Boston, MA (US)

(73) Assignees: UNIVERSITE DE STRASBOURG, Strasbourg (FR); CENTRE NATIONAL DE LA RECHERCHE SCIENTIFIQUE, Paris (FR); INSTITUT NATIONAL DE LA SANTE ET DE LA RECHERCHE MEDICALE, Paris (FR)

(*) Notice: Subject to any disclaimer, the term of this patent is extended or adjusted under 35 U.S.C. 154(b) by 769 days.

(21) Appl. No.: 16/336,488

(22) PCT Filed: Sep. 26, 2017

(86) PCT No.: PCT/EP2017/074387
§ 371 (c)(1),
(2) Date: Mar. 26, 2019

(87) PCT Pub. No.: WO2018/055206
PCT Pub. Date: Mar. 29, 2018

(65) Prior Publication Data
US 2019/0225950 A1    Jul. 25, 2019

(30) Foreign Application Priority Data
Sep. 26, 2016 (EP) .................... 16306232

(51) Int. Cl.
C12N 9/12      (2006.01)
C12N 7/00      (2006.01)
(Continued)

(52) U.S. Cl.
CPC ............ *C12N 15/52* (2013.01); *A61K 31/427* (2013.01); *A61K 31/4439* (2013.01);
(Continued)

(58) Field of Classification Search
None
See application file for complete search history.

(56) References Cited

U.S. PATENT DOCUMENTS

2018/0256749 A1* 9/2018 Green .................. A61K 48/005

FOREIGN PATENT DOCUMENTS

WO    WO-2004009622 A2 *  1/2004  ............. C07K 14/47

OTHER PUBLICATIONS

Imai et al., Identification and Characterization of a Novel Human Type II Diacylglycerol Kinase, DGKk (JBC, 2005, 280:39870-39881) (Year: 2005).*

(Continued)

*Primary Examiner* — Arthur S Leonard
(74) *Attorney, Agent, or Firm* — Saliwanchik, Lloyd & Eisenschenk

(57) ABSTRACT

The present invention relates to a nucleic acid coding for a human DGKk protein lacking a functional Proline Rich Region and/or a functional EPAPE repeated Region, and to its use in the treatment of fragile X syndrome in a patient in need thereof.

13 Claims, 9 Drawing Sheets

Specification includes a Sequence Listing.

(51) Int. Cl.
   A61K 48/00      (2006.01)
   C12N 15/52      (2006.01)
   A61K 31/427     (2006.01)
   A61K 31/4439    (2006.01)
   A61K 31/506     (2006.01)
   A61K 38/45      (2006.01)
   A61K 38/00      (2006.01)
   C12N 15/864     (2006.01)
   A61K 31/426     (2006.01)

(52) U.S. Cl.
   CPC .......... *A61K 31/506* (2013.01); *A61K 38/45* (2013.01); *A61K 48/0066* (2013.01); *C12N 7/00* (2013.01); *C12Y 207/01107* (2013.01); *A61K 31/426* (2013.01); *A61K 38/00* (2013.01); *A61K 48/00* (2013.01); *C12N 9/1205* (2013.01); *C12N 15/8645* (2013.01); *C12N 2750/14143* (2013.01)

(56) References Cited

OTHER PUBLICATIONS

Farshbaf et al., Peroxisome proliferator activated receptor gamma (PPARγ) as a therapeutic target for improvement of cognitive performance in Fragile-X (Med Hyp, 2014, 82:291-294) (Year: 2014).*

Van der Zanden et al. Common variants in DGKK are strongly associated with risk of hypospadias (Nature Genetics, 2011, 43:48-50) (Year: 2011).*

GenBank ID EAW89919. diacylglycerol kinase, kappa, partial [Homo sapiens] (submitted Jul. 5, 2005, pp. 1-2) (Year: 2005).*

NCBI ID NG_033143 Homo sapiens diacylglycerol kinase kappa (DGKK), RefSeqGene on chromosome X (submitted 2005, pp. 1-22) (Year: 2005).*

Tanguy et al. ystemic AAVrh10 provides higher transgene expression than AAV9 in the brain and the spinal cord of neonatal mice (Front Mol Neuro, 2015, 8:1-10) (Year: 2015).*

Database EMBL [Online] Accession No. JV052157, "TSA: Macaca mulatta Mamu_409904 mRNA sequence" Apr. 22, 2012, p. 1, XP002767990.

Database EMBL [Online] Accession No. JV642685, "TSA: Macaca mulatta Mamu_456756 mRNA sequence" May 17, 2012, pp. 1-2, XP002767991.

Database EMBL [Online] Accession No. BC075627, "Mus musculus diacylglycerol kinase kappa, mRNA (cDNA clone MGC:92983 IMAGE:6852516), complete cds." Jul. 2, 2004, pp. 1-3, XP002767992.

Tabet, R et al. "Fragile X Mental Retardation Protein (FMRP) controls diacylglycerol kinase activity in neurons" *PNAS*, May 27, 2016, pp. E3619-E3628.

Mcmahon, A. C. et al. "Promiscuous or discriminating: Has the favored mRNA target of Fragile X Mental Retardation Protein been overlooked?" *PNAS*, Jun. 28, 2016, pp. 7009-7011, vol. 113, No. 26.

Tabet, R. et al. "Fragile X syndrome: Are signaling lipids the missing culprits?" *Biochimie*, 2016, pp. 188-194, vol. 130.

He, C. X. et al. "The trouble with spines in fragile X syndrome: density, maturity and plasticity" *Neuroscience*, 2013, pp. 120-128, vol. 251.

Zimin, A. V. et al. "A new rhesus macaque assembly and annotation for next-generation sequencing analyses" *Biology Direct*, 2014, pp. 1-15, vol. 9, No. 20.

Written Opinion in International Application No. PCT/EP2017/074387, dated Dec. 7, 2017, pp. 1-8.

* cited by examiner

SEQUENCE LISTING

<160> NUMBER OF SEQ ID NOS: 9

<210> SEQ ID NO 1
<211> LENGTH: 3816
<212> TYPE: DNA
<213> ORGANISM: Homo sapiens
<220> FEATURE:
<221> NAME/KEY: Proline Rich Region
<222> LOCATION: (70)..(132)
<220> FEATURE:
<221> NAME/KEY: EPAPE repeated region
<222> LOCATION: (142)..(539)

<400> SEQUENCE: 1

| | | | | | |
|---|---|---|---|---|---|
| atggaccgcg | gagctgccgc | agcccagggc | actgccccgc | ctcaggatgg agagcagccc | 60 |
| gctgagtctc | cagagcctcc | gccgccttgg | ccgccgccgc | caccaccacc ggctccgccg | 120 |
| ccggctccgc | cgctgctctc | cgaggcttcg | ccagaaccca | taccagagcc ctgtccagag | 180 |
| cttgctccag | gtccctgtcc | agaggcgacc | tcagaatcag | ccacagaact gtacacagaa | 240 |
| ccgaccccag | aaccagccac | agagccggcc | tcagaaccgg | ccccagaacc tgccacagag | 300 |
| ccggccccag | aacctgccac | agagccggcc | ccagaaccgg | ccccagaacc tgccacagag | 360 |
| tctgccccag | agccgactcc | agaacctgcc | ctagagtcgg | tcccagagcc ggccccagag | 420 |
| ctgactccaa | agttgccccc | agagctgccc | cagagccga | cccagaaacc tgtgacagag | 480 |
| ctggccccag | agttctgccc | tgaggcggct | ccagagttcc | gtccaagtcc agcaccatgt | 540 |
| ctattgcaat | gtccggtgga | cactcgagag | agaggtctaa | agacctcgcc atcgccatcg | 600 |
| ccatcgccat | cgcccagaac | gccaatgtcg | tggtccagaa | taaagaaaat attgaaggaa | 660 |
| ggacctatgc | tgaagaactg | taactctttc | aagagatgga | agcttagata ttttctggtt | 720 |
| caaggacaga | agctctactt | tgcacaccat | cccgcgtttg | cacactttga aacgattgat | 780 |
| ctgtctcaag | ccactgtggc | agaaagcagc | tgtagaaacc | tttgccacag tttttgtgtt | 840 |
| attacaccac | aacgaaaaat | cactctggct | gcacccaacc | ggaaagacat ggaagaatgg | 900 |
| attaacatca | taaaaaccat | ccaacaggga | gaaatttata | agatacctgc agcagaaaac | 960 |
| aacccttttc | ttgttggaat | gcattgttgg | tactccagtt | acagccaccg gacccagcac | 1020 |
| tgcaatgttt | gtcgagagag | cattcctgcc | ttatctagag | atgccatcat ctgtgaagtg | 1080 |
| tgcaaagtga | atctcacag | attgtgtgct | ttgagagcaa | gcaaagactg caagtggaat | 1140 |
| acattgtcta | tcactgatga | cctccttctg | cctgcagatg | aagtaaacat gccccatcaa | 1200 |
| tgggtagaag | gaaacatgcc | tgtcagctct | cagtgtgcag | tgtgtcatga gagctgtggc | 1260 |
| agttatcaaa | gacttcaaga | cttccgctgc | ctgtggtgta | attctacggt gcatgatgac | 1320 |
| tgtaggagac | ggttttccaa | ggaatgttgc | ttcagaagcc | atcgctcatc agtcattcct | 1380 |
| cccactgctc | taagcgaccc | caaaggcgat | ggccaattag | tagtatcttc agacttctgg | 1440 |
| aatcttgatt | ggtcatcagc | ctgttcatgt | cccttgctca | tcttcatcaa ctccaaaagt | 1500 |
| ggcgatcatc | aggggatcgt | cttcctccga | aaattcaagc | aataccttaa cccatctcaa | 1560 |
| gtgttcgact | tattgaaggg | tggacctgaa | gcagggctgt | ctatgttcaa gaactttgct | 1620 |
| cgctttcgca | ttctggtttg | tggtggagat | ggcagcgtga | gctgggtctt atctctgatt | 1680 |
| gatgcctttg | gattacatga | aaagtgtcag | ttggcagtca | tcccacttgg aaccggcaat | 1740 |
| gatctggctc | gtgttctggg | ctggggtgca | ttctggaaca | aaagcaagtc acctctggac | 1800 |
| atcctcaaca | gagtggagca | ggctagtgtg | aggatcctag | acagatggag tgtgatgatt | 1860 |
| cgtgagactc | ccagacaaac | cccgctgcta | aaaggacagg | ttgaaatgga tgtaccacga | 1920 |

```
tttgaggctg ctgccatcca acacttagaa tctgcagcca ccgagttgaa caaaatcctg    1980
aaggccaagt accccacaga gatgatcatc gcaaccagat tcttgtgttc agctgtggaa    2040
gattttgtgg ttgatattgt aaaggcctgg ggtcagataa aacagaacaa cactgcaata    2100
gtgtctgtga ttttgaaaag tgacttaatg tatgataggc tcagtgtcct gatcgatgtc    2160
ctggctgagg aggcagcagc tacttctgct gaaaaaagtg ctacagaata tgcagacagc    2220
agcaaggcag ataggaagcc cttcattcct caaatagacc acatagccaa gtgcaagttg    2280
gagctggcta caaaggccca gagtctccag aaatccttga aactcatcat atttcaagtt    2340
gaacaagctc tggatgagga agcagacag acaatatctg ttaagaactt tagttcaact    2400
ttcttcctgg aagatgaccc agaagatatt aaccagacaa gcccacgacg ccgttctcgt    2460
cgtggcactt tgtcttctat atcttctctc aaaagtgagg acctgacaa ccttaacttg    2520 gatcacttac attttacacc tgaatctata cgcttcaaag aaaaatgtgt catgaacaac    2580
tacttcggaa ttggactgga tgctaaaatt tctctggact tcaacaccag aagagatgaa    2640
cacccagggc aatacaatag ccgccttaag aacaagatgt ggtatggcct tctgggaacc    2700
aaagaacttt tgcagcgctc ttacaggaaa ctggaagaac gagtgcattt ggagtgtgat    2760
ggagaaacca tctccttgcc aaacctgcaa ggcattgtag tgctcaacat taccagctat    2820 gctgaggta tcaacttctg gggaagcaac acagcaacca cggaatatga ggctcctgca    2880
atcgatgatg ggaaactgga ggtggtggca atctttggtt ctgtgcagat ggcaatgtcc    2940
cgtatcatca acctgcatca tcatcgcatt gcccagtgcc atgaggtgat gataaccatt    3000
gatggtgaag aaggtatccc agtgcaggtg gatggggagg cctggattca gagaccaggc    3060
cttatcaaaa ttagatacaa gaacgctgcc cagatgctga caagagatcg ggactttgag    3120
aactcaatga aaatgtggga atacaagcat actgaaattc aagctgcccc tcaaccccag    3180
ctggacttcc aggactctca agagagcctc tctgacgagg agtatgccca gatgcagcac    3240
ttagctcggc ttgcagaaaa cctcatcagc aaacttaatg acctgagcaa gatccaccag    3300
catgtgtctg tcctcatggg ttctgtgaat gccagcgcta acatcctgaa tgatatattt    3360
tacggccaag acagtggcaa tgagatgggt gcagcttcct gtattcccat tgaaactcta    3420
agcagaaatg atgccgtaga tgttacattt agtcttaaag gtctctacga tgacaccaca    3480
gctttcctgg atgaaaagct gctgagaagt gctgaggatg agactgcact acaaagcgcc    3540
ctggatgcca tgaataagga gttcaaaaag ctatctgaga ttgactggat gaatccaatc    3600
tttgttccag aggaaaaatc ttcggacact gacagtagaa gcctcaggct gaaaattaag    3660
ttccccaaat tgggaaagaa aaaggtagaa gaggaacgca agcctaaatc aggccagagt    3720
gtccagagtt ttattggcaa tttatggcac cgcagacatc gtgaagatga agcagagggt    3780
gatgatcctc taacaccatc gagatctcaa ctgtag                              3816
```

<210> SEQ ID NO 2
<211> LENGTH: 30
<212> TYPE: DNA
<213> ORGANISM: Artificial Sequence
<220> FEATURE:
<223> OTHER INFORMATION: Primer

<400> SEQUENCE: 2
gcagctagct ccttgaaagc tggaaggaga                                       30

<210> SEQ ID NO 3

```
<211> LENGTH: 37
<212> TYPE: DNA
<213> ORGANISM: Artificial Sequence
<220> FEATURE:
<223> OTHER INFORMATION: primer

<400> SEQUENCE: 3
aatagaatgc ggccgccagc ttcaacagca cttgtag                                    37

<210> SEQ ID NO 4
<211> LENGTH: 58
<212> TYPE: DNA
<213> ORGANISM: Artificial Sequence
<220> FEATURE:
<223> OTHER INFORMATION: primer

<400> SEQUENCE: 4
ttctcaacta tacccatacg atgttccaga ttacgcttag tccttgaaag ctggaagg            58

<210> SEQ ID NO 5
<211> LENGTH: 60
<212> TYPE: DNA
<213> ORGANISM: Artificial Sequence
<220> FEATURE:
<223> OTHER INFORMATION: primer

<400> SEQUENCE: 5
tcaaggacta agcgtaatct ggaacatcgt atgggtatag ttgagaactt gaaggtgttg         60

<210> SEQ ID NO 6
<211> LENGTH: 21
<212> TYPE: DNA
<213> ORGANISM: Artificial Sequence
<220> FEATURE:
<223> OTHER INFORMATION: shRNA

<400> SEQUENCE: 6
ggaatgcact actggtattc c                                                    21

<210> SEQ ID NO 7
<211> LENGTH: 19
<212> TYPE: DNA
<213> ORGANISM: Artificial Sequence
<220> FEATURE:
<223> OTHER INFORMATION: shRNA

<400> SEQUENCE: 7
gcgcttagct gtaggattc                                                       19

<210> SEQ ID NO 8
<211> LENGTH: 8085
<212> TYPE: DNA
<213> ORGANISM: Mus musculus
<220> FEATURE:
<221> NAME/KEY: 5'UTR
<222> LOCATION: (1)..(158)
<220> FEATURE:
<221> NAME/KEY: Proline Rich Region
<222> LOCATION: (231)..(350)
<220> FEATURE:
<221> NAME/KEY: EPAPE repeated region
<222> LOCATION: (351)..(857)
<220> FEATURE:
<221> NAME/KEY: Tag HA
<222> LOCATION: (4209)..(4235)
<220> FEATURE:
<221> NAME/KEY: 3'UTR
<222> LOCATION: (4239)..(8085)
```

```
<400> SEQUENCE: 8
cttagacctc agagctgcgc tagccatgga gcgaagcggg tgcaaagttt ggcaccctgc      60
aaagggatgt cagataggag tgggtggacc gcccaagggc tctttagccc tctaagctta     120
gggaccccgg ctgcctggac ctcagacggt gtgctgcaat ggacggtgta gattcggtgg     180
cccagggcac tgcccagcct caggatggag agcagcctgc tgagtcccca gagccgccgc     240
cgccacctcc cgctccgccg cccgcccac cgctccggc ccaccgcct ccggcccac        300 cgccgccggc cccaccaccg cctgctcctc caccattccc tgagccttct ccagaaccag     360
taccagagcc tgctctggga ccctgtccag aggcgactcc agaaccagcc acagaaacag     420
acgcaaaatc aaccccagag ccggccccga agccggactc agaaccggac tcggacccgg     480
ccctcgaacc agactcagag ccggcccag agccggaccc cgaaccagac tcagagccgg     540
ccccagagcc ggaccccgaa ccagactcag agccggcccc agagccggac cccgaaccag     600
actcagagcc ggccccagag ccggaccccg aaccagactc agagccggcc cagagccgg     660 accccgaacc agactcagag ccggcccag agccggaccc cgaaccagac tcagaaccgg     720
ccccagaacc agtctcagag ccggcccag aacttgtccc agagctggcc tcggagccgg     780
ccccagaacc tgtcctagag ccaaccctag agttggcctc agaactggcc ctagaaccag     840
ccccagatcc tgccatggag agggccccag agtcctggcc agagccaact ccagagtcct     900
gtctaagaat gagtccagca ctacatctgt tgcaggtagt tcctggagag aaaagtggaa     960
cagcatctcc agtgctattg ccattgccgt cgcccaaacc gccaataacg tggtccagaa    1020
taaagaaaat actgaaggaa ggaccctgc tgaagaactg taactccttc agaagatgga     1080
agcttagata ctgtctggtt caagggcaga agctccactt tgcacaccat ccttcgtttg    1140
cacactttga acaattgat ctgtctcaag ttgttttggc tgaaagtagc tgcagaaatc    1200
tttgccatgg tttttgtgtt atcacaccac atcgaaaagt gtctctagtt gcacccactc    1260
ggcaagacat ggaagaatgg attaacatca taaaaactgt ccaacaagga gaaatccgtc    1320
agatccctgc agccgaaaac aaccccttc ttgtcggaat gcactactgg tattccagta    1380
gtaatccccg gagtcacttc tgcaatgttt gtcgagagaa cattcctgct ttatctcgag    1440
atgccgtcac ctgtgaagtc tgtcaggtga atctcataa attctgtgct ttgagagcaa    1500
acaaagactg taaatggaat actttatccg tgactgatga ccttcttcta cccgctgatg    1560
aaatacaaac aatgccgcat cagtgggtag aaggaaatat acccgctggc tctcaatgtg    1620
tcgtatgtca caagagctgc ggtagtcatc acagacttca ggatttccgc tgcctctggt    1680
gcggctctac ggtgcacggg gcctgccaga agcggttttc caaggaatgt tccttcggaa    1740
gtcgtcgctc gtccatcgtg ccaccaacgg cactgagcga ccctagggc gatggccagc    1800 tagtagtatc gcctgacttc tggaatcttg actggccact gacttgttcc tgtcccttgc    1860
tcatcttcat caactctaaa agtggagatc atcaagggat catctttctc cggaaattca    1920
aacaatacct taatccgtct caagtattcg acctggcgaa gggtggacct gaagcaggca    1980
tcgctatgtt caagaacttt gcccgttttc gtgttctggt tgtggtgga gatggcagtg    2040 tgagctgggt cttgtctacg attgatgcct atggattgca tgataggtgt cagctggcga    2100
tcatcccact tggaactggt aatgatctcg ctcgtgtcct gggctgggga gcagtctgga    2160
gtaaaggcac atcaccactg atattctca gcagagtgga gcaggctcac gtgaggattt    2220
tagacagatg gagtgtgatg atccgtgaga ccccccagaca agccccgctg ctgaaaggac    2280
aagtggcaat ggatatacca agatttgagg ctgctgccat caagaacgta gagtctgcaa    2340
```

```
ccactgagtt gaacaaaatt ctgaaggcca aatatcccac ggagatggtc atcgccacaa    2400
gattcctgtg ctcagcagtg gaagattttg tggaagatat tgtaaaggcc tggcaccaaa    2460
taaaacagaa cagcacagca gtggagtctg tgattttgaa aagcgactta atgtatgata    2520
aactcagtgt ccttattgat ctcctggctg aggatgcagt agctgcctcc gctgagagga    2580
cagccacagc atatggaagc agaagccaag cagatggaaa acccttcgtg cctcaactag    2640
accacatagc aagggccaaa ctggagttgg ctgaaagggc tcagaaactc cagcagtcct    2700
tgaaactcat catattccag gtcgaacaag ttctggatga agaaagcaga cagagcttat    2760
cagttaagaa ctttacttca tctttgttcc tgggagacgg agacgacgac gactcagatg    2820
actatgatca gagccctaga caccgttctc gttgtgacat cttatgttct ataccttctc    2880
tgagaaatga agacctagat aaccttgact agaacacttt acacattgca cctgaaacga    2940
tacgcttcaa agaaaagtgt gtcatgaaca actactttgg aattggacta gacgcaaaaa    3000
tctctctgga gtttaattcc agaagagaag aacatccaga acaatacaat agccgcctca    3060
agaacaaaat atggtatggt cttctgggaa gcaaggaatt actgcaacgc tcttacagga    3120
aattggaaga gcgaatacac ctcgagtgtg atggagaagc tgtctccttg ccaaaccttc    3180
aaggcatcgt agtgctcaac attacgagct acgctggagg cgtcaacttt tggggaagaa    3240
acagagcaac cacagaatat gatgtccctg caatcaatga tgggaagcta gaggttgtgg    3300
caatctttgg ttctgtgcag atggccatgt ctcgtatcgt caacctgcaa caacatcgaa    3360
ttgcgcagtg ccatgaggtg gtaataacta ttgatggtga agacggtgtc cctgtgcaag    3420
tggatgggga agcctggatt cagaagccag gccttatcaa gattaaatac aagaatgttg    3480
cccagatgtt gatgagagat agggactttg agaactcaat gaaaacctgg gaatctaagc    3540
atactgaaat ccaagctgtc caaccacccc acctggattt ccaggaatct caagacagcc    3600
tctctgatgg agagtatgcc cagatgcagc acttggctcg gcttcagaaa acctcatta    3660 gcagacttac tgacctaagc aaggtccacc agcacgtgtc tgtcctcatg gattctgtga    3720
atgccagtgc taacatactg aatgatgtgt tctatagcca agacagtggt aacgaagcag    3780
gcgcagcttc ctgcattccc attgagactc taagcagaac tgatgcagta gatgttacat    3840
ttagtcttaa agggctctac gatgacacca agctttcct ggatgaaaac ttgttgagag    3900
atgctgagga tcgggccatg ctacaaactg ccttggatgc catgaataca gagttaagaa    3960
ggatactggc aattggctgg ctgagtcaaa tcttctttcc agaggaacag gcttctgaca    4020
ctcgcagttt aagtcgtagg tttagaataa aattccccaa gctggggaag aagaaacaac    4080
gagaagaggg agaaaagcct aaatcaagcc aaagattccc tggttttctt ggcaagttct    4140
ggcgtcgaag aaatcgtagc aatcgagcaa agctgatga ccctccaaca ccttcaagtt    4200
ctcaactata cccatacgat gttccagatt acgcttagtc cttgaaagct ggaaggagag    4260
ctctcaacac agaattctac taaaaactct caagacctca agaaggctg aactaaatta    4320 tttctgaaca acatgagca ccaccaagaa agaccctcca aatccttata ctaatatgtt    4380
ttccccagac ttaatcagat cacccttagag ggttacattt ttctcgttgg ccaaagattc    4440
ttgttccgag ttgtcttgtt cagttcttct cgttgtgtac cttgggcaac tacagtgttt    4500
attggggaca ggctctctat gaatggcctg ggagctatga gaatgtatgg gagtgcatct    4560
cgttaggaaa tattgaatg gggggtcttt cacttggaga gaaactgttg acaccaagga    4620
ataaatgagt gaccaagtct cagaaagatg aggaagggga agggtgtcca ggcttagttg    4680
```

| | |
|---|---|
| tgtttctcct ccaatccctg ccaattgcaa cttgaatttc aaaagatggc tcctagttgg | 4740 |
| cttaagaaga tgagaacaag gtcctggggc ttgtccactc atctgttaca atgactatgt | 4800 |
| gaatcttttc ttatagatat agaactctcc tcttctctct ttcctttctc ctctcatttc | 4860 |
| ctcttctctc ctctaccacc tcttatctcc tctacatctc ttctctctcc tctcacttct | 4920 |
| ctctttctcc acctccttct aatttctttc ccctttcttt cctttccatc tctccttctc | 4980 |
| ttccactttc ctctattact cccttatctcc ccataaactc ttcgtgtttt tccatgtgta | 5040 |
| catgtatgtc tttgcacatg tccaggtggt gctctcgtgg ctgggtgggc ccactggttg | 5100 |
| gaactcaccc ctcatggcaa ccatacaggc tcctgtactt tgccttgat cccagcctgc | 5160 |
| atgtctccat ggagtgcttg cctgcattct cgctggattt tttaactaaa tgttttgccg | 5220 |
| ctgtgctgca gtatagatta tatacagaga cataaagatg tacatatata tacatatata | 5280 |
| ttttaagaa ctgaaaatac aactcgacct ctaagtgacc ctctaattta ttatgataac | 5340 |
| ccaggaatcc ctcctcatcc ctattaccct atacacatat atactctacc aactgcccta | 5400 |
| gttcttggtg gagcttctaa tcttttggtg cattttttag tgtcttagaa gtagctgggg | 5460 |
| tctatatatc ccagctaatt ctgacatcca cttctgagcc aggccacaga agggaacaa | 5520 |
| aaacaccaat gccctgccaa aagggcccag ctggcatgct gccatttagc tctgtttctc | 5580 |
| ctggctctac atcagtaact gcccaagcta tatcaccctc ctccccaata aaaagatgtc | 5640 |
| aaagagctct acccttaaa tgtctaagtc agggtctacc tgacaataaa accacagccc | 5700 |
| atgcccctcc ccaaaagctt aatctgggcc tgcagctatt agataagctg ttgggtcact | 5760 |
| cctcaaatta tcttcaaatc tcatatctta cccctcccc ccccccccag agtataagag | 5820 |
| aggcagtcag agtgaccaga aagaacattg atctgggaaa agaaaggcga aaagcctctg | 5880 |
| cttccccact gttctgcttc caaggtggtt ttcatgaaca tagtcggtct ccaatctcag | 5940 |
| tcaagtaaat ctgccgagag tgcagtgctc agaaagaagg tctctggtct acctcctctt | 6000 |
| cacccctcaag tcgcaccttt tggaacaagt cccttcccac ttatcaagaa aaagatccag | 6060 |
| aaaactgccc ttttctcact gctcagccaa acttagcgtg ctcaattacc ttgctcagtc | 6120 |
| caatggctgg ttcactgagg tgcacaatcc agacttcgat cactggttct taactttcta | 6180 |
| gaacaccacc agcctaaccc acttaaacca gctgcctgtg ttccacctct tcaagggtga | 6240 |
| gaaaaagaga ctaacaatgg ggtagtcccc aaacatctga tagctgtgcc aaacaaaaaa | 6300 |
| acaaaaaaca aaaaaaaat gtcctcgctc tacaactgga gaagaaattc aatgggaaaa | 6360 |
| gatgacagaa aacgtgtaag actcaaataa cagaatgtgt acgtgttgac agtgtatgta | 6420 |
| tttgagggga gtgctgttgc agtgtctctg gttttctctt atgcctcttt cttcccagga | 6480 |
| ggaggtatct gatcaaacca ccaaggttcc tccttggttg caggaatgaa tacctgcaca | 6540 |
| gacacactca cagagttggg atccatctta aattttctca gaggagtctt tcccaaggat | 6600 |
| catgtataaa taagcaaatt taaggaaaca gaaggaaatc ttaggaaacc gtagccttat | 6660 |
| cttggtagtg actaagcagg gctatgtctt gtaattattt ttatcacaat gatagtcaac | 6720 |
| tggaacagga ccccatctct gcctattttg ctgaagtact actgtaggtc tttgtgtact | 6780 |
| gcaatgctgc tgttgctcta ttgtaccatc tgaattccca ctcactttcc ctgttccccc | 6840 |
| acctgagtca gagtgctact gaatgacacc cataggatgg ggacttgaac caaatgtgga | 6900 |
| gcaaaactga taagctaaaa aaccaacttg gcttgttaaa atggtccaga tatcattagt | 6960 |
| taccgatttc ttttcctgag aaaggaagat gacatgctaa gaacgtgttc acacatctac | 7020 |
| aaagtaagaa gggatctccc tccctcccta gctacctacc atctcccct ctcctccctc | 7080 |

-continued

```
tttctctctc ccccacctcc tctgaagtta acttagcccc taagaacatg ggctcctttc      7140
aagatttcat tgttgactat ttgaagaact acagttgttc aggtggtggg actggaaacc      7200
aagtatctgc cacagttatg tgcagaaatc attaagaatc aaaactctgg ggtttgattg      7260
tgtctttggt agtactttct gcagaattga ttgaatggct aattcttggc cagaaggaca      7320
ttagagaagg aaaaatctga atagcgttaa gctgccacca accacttctg gcattgatac      7380
tataggaggt caccagctat cctgtaaagc cctctgttac agcaaagaag gttaagagaa      7440
gaataaaaag taataaaagg tgaccagaag aaatttgggg ggatcaacat catcttccca      7500
caggacacag tagaatttta gttgtataac agatggaaac tattaccaaa gagatcagac      7560
ctcattcaca ctttcccatt ggatacggga ccttgattgg ctttatggtt atggagttgc      7620
attcgtctgc taatctgtaa tacattgttg ctttctattc tgtgttctgt gttttctcaa      7680
aggccctgca aaataagtag cagggccagg gcctggttag gggaggaggc tggaatagtc      7740
atggaataac agaaaaaaat gcagaaggaa aagatccaca aagtgtgcct attccttta       7800 gccctcccca caaatggaa caccagtcct cacaattgta attgcttctt aaaatatttt       7860
aataaatgga taaatagcat caatatctac gtcttctcac ttctttcaac ttggagggg        7920 tgatagttaa atggggctgg atgttagtta ttggattggg gtggtctttt aagctctcaa      7980
taggctacca acaggtacca gaggcaggaa agactaggca gcaaaacaca aaccaggact      8040
ggcccatcat tgtgatttta atactacaag tgctgttgaa gctgg                     8085
```

```
<210> SEQ ID NO 9
<211> LENGTH: 1271
<212> TYPE: PRT
<213> ORGANISM: Homo sapiens

<400> SEQUENCE: 9

Met Asp Arg Gly Ala Ala Ala Gln Gly Thr Ala Pro Pro Gln Asp
1               5                   10                  15

Gly Glu Gln Pro Ala Glu Ser Pro Glu Pro Pro Pro Trp Pro Pro
                20                  25                  30

Pro Pro Pro Pro Pro Ala Pro Pro Ala Pro Pro Leu Leu Ser Glu
            35                  40                  45

Ala Ser Pro Glu Pro Ile Pro Glu Pro Cys Pro Glu Leu Ala Pro Gly
    50                  55                  60

Pro Cys Pro Glu Ala Thr Ser Glu Ser Ala Thr Glu Leu Tyr Thr Glu
65                  70                  75                  80

Pro Thr Pro Glu Pro Ala Thr Glu Pro Ala Ser Glu Pro Ala Pro Glu
                85                  90                  95

Pro Ala Thr Glu Pro Ala Pro Glu Pro Ala Thr Glu Pro Ala Pro Glu
            100                 105                 110

Pro Ala Pro Glu Pro Ala Thr Glu Ser Ala Pro Glu Pro Thr Pro Glu
        115                 120                 125

Pro Ala Leu Glu Ser Val Pro Glu Pro Ala Pro Glu Leu Thr Pro Glu
    130                 135                 140

Val Ala Pro Glu Leu Ala Pro Glu Pro Thr Pro Glu Pro Val Thr Glu
145                 150                 155                 160

Leu Ala Pro Glu Phe Cys Pro Glu Ala Ala Pro Glu Phe Arg Pro Ser
                165                 170                 175

Pro Ala Pro Cys Leu Leu Gln Cys Pro Val Asp Thr Arg Glu Arg Gly
            180                 185                 190
```

-continued

```
Leu Lys Thr Ser Pro Ser Pro Ser Pro Ser Pro Arg Thr Pro
        195             200             205
Met Ser Trp Ser Arg Ile Lys Lys Ile Leu Lys Glu Gly Pro Met Leu
    210             215             220
Lys Asn Cys Asn Ser Phe Lys Arg Trp Lys Leu Arg Tyr Phe Leu Val
225             230             235             240
Gln Gly Gln Lys Leu Tyr Phe Ala His His Pro Ala Phe Ala His Phe
                245             250             255
Glu Thr Ile Asp Leu Ser Gln Ala Thr Val Ala Glu Ser Ser Cys Arg
                260             265             270
Asn Leu Cys His Ser Phe Cys Val Ile Thr Pro Gln Arg Lys Ile Thr
            275             280             285
Leu Ala Ala Pro Asn Arg Lys Asp Met Glu Glu Trp Ile Asn Ile Ile
        290             295             300
Lys Thr Ile Gln Gln Gly Glu Ile Tyr Lys Ile Pro Ala Ala Glu Asn
305             310             315             320
Asn Pro Phe Leu Val Gly Met His Cys Trp Tyr Ser Ser Tyr Ser His
                325             330             335
Arg Thr Gln His Cys Asn Val Cys Arg Glu Ser Ile Pro Ala Leu Ser
                340             345             350
Arg Asp Ala Ile Ile Cys Glu Val Cys Lys Val Lys Ser His Arg Leu
            355             360             365
Cys Ala Leu Arg Ala Ser Lys Asp Cys Lys Trp Asn Thr Leu Ser Ile
        370             375             380
Thr Asp Asp Leu Leu Leu Pro Ala Asp Glu Val Asn Met Pro His Gln
385             390             395             400
Trp Val Glu Gly Asn Met Pro Val Ser Ser Gln Cys Ala Val Cys His
                405             410             415
Glu Ser Cys Gly Ser Tyr Gln Arg Leu Gln Asp Phe Arg Cys Leu Trp
                420             425             430
Cys Asn Ser Thr Val His Asp Asp Cys Arg Arg Arg Phe Ser Lys Glu
            435             440             445
Cys Cys Phe Arg Ser His Arg Ser Ser Val Ile Pro Pro Thr Ala Leu
        450             455             460
Ser Asp Pro Lys Gly Asp Gly Gln Leu Val Val Ser Ser Asp Phe Trp
465             470             475             480
Asn Leu Asp Trp Ser Ser Ala Cys Ser Cys Pro Leu Leu Ile Phe Ile
                485             490             495
Asn Ser Lys Ser Gly Asp His Gln Gly Ile Val Phe Leu Arg Lys Phe
            500             505             510
Lys Gln Tyr Leu Asn Pro Ser Gln Val Phe Asp Leu Leu Lys Gly Gly
        515             520             525
Pro Glu Ala Gly Leu Ser Met Phe Lys Asn Phe Ala Arg Phe Arg Ile
    530             535             540
Leu Val Cys Gly Gly Asp Gly Ser Val Ser Trp Val Leu Ser Leu Ile
545             550             555             560
Asp Ala Phe Gly Leu His Glu Lys Cys Gln Leu Ala Val Ile Pro Leu
                565             570             575
Gly Thr Gly Asn Asp Leu Ala Arg Val Leu Gly Trp Gly Ala Phe Trp
            580             585             590
Asn Lys Ser Lys Ser Pro Leu Asp Ile Leu Asn Arg Val Glu Gln Ala
        595             600             605
Ser Val Arg Ile Leu Asp Arg Trp Ser Val Met Ile Arg Glu Thr Pro
```

-continued

```
            610                 615                 620
Arg Gln Thr Pro Leu Leu Lys Gly Gln Val Glu Met Asp Val Pro Arg
625                 630                 635                 640

Phe Glu Ala Ala Ala Ile Gln His Leu Glu Ser Ala Ala Thr Glu Leu
                645                 650                 655

Asn Lys Ile Leu Lys Ala Lys Tyr Pro Thr Glu Met Ile Ile Ala Thr
                660                 665                 670

Arg Phe Leu Cys Ser Ala Val Glu Asp Phe Val Val Asp Ile Val Lys
            675                 680                 685

Ala Trp Gly Gln Ile Lys Gln Asn Asn Thr Ala Ile Val Ser Val Ile
        690                 695                 700

Leu Lys Ser Asp Leu Met Tyr Asp Arg Leu Ser Val Leu Ile Asp Val
705                 710                 715                 720

Leu Ala Glu Glu Ala Ala Thr Ser Ala Lys Ser Ala Thr Glu
                725                 730                 735

Tyr Ala Asp Ser Ser Lys Ala Asp Arg Lys Pro Phe Ile Pro Gln Ile
                740                 745                 750

Asp His Ile Ala Lys Cys Lys Leu Glu Leu Ala Thr Lys Ala Gln Ser
            755                 760                 765

Leu Gln Lys Ser Leu Lys Leu Ile Ile Phe Gln Val Glu Gln Ala Leu
770                 775                 780

Asp Glu Glu Ser Arg Gln Thr Ile Ser Val Lys Asn Phe Ser Ser Thr
785                 790                 795                 800

Phe Phe Leu Glu Asp Asp Pro Glu Asp Ile Asn Gln Thr Ser Pro Arg
                805                 810                 815

Arg Arg Ser Arg Arg Gly Thr Leu Ser Ser Ile Ser Ser Leu Lys Ser
            820                 825                 830

Glu Asp Leu Asp Asn Leu Asn Leu Asp His Leu His Phe Thr Pro Glu
            835                 840                 845

Ser Ile Arg Phe Lys Glu Lys Cys Val Met Asn Asn Tyr Phe Gly Ile
        850                 855                 860

Gly Leu Asp Ala Lys Ile Ser Leu Asp Phe Asn Thr Arg Arg Asp Glu
865                 870                 875                 880

His Pro Gly Gln Tyr Asn Ser Arg Leu Lys Asn Lys Met Trp Tyr Gly
                885                 890                 895

Leu Leu Gly Thr Lys Glu Leu Leu Gln Arg Ser Tyr Arg Lys Leu Glu
            900                 905                 910

Glu Arg Val His Leu Glu Cys Asp Gly Glu Thr Ile Ser Leu Pro Asn
        915                 920                 925

Leu Gln Gly Ile Val Val Leu Asn Ile Thr Ser Tyr Ala Gly Gly Ile
930                 935                 940

Asn Phe Trp Gly Ser Asn Thr Ala Thr Thr Glu Tyr Glu Ala Pro Ala
945                 950                 955                 960

Ile Asp Asp Gly Lys Leu Glu Val Val Ala Ile Phe Gly Ser Val Gln
                965                 970                 975

Met Ala Met Ser Arg Ile Ile Asn Leu His His Arg Ile Ala Gln
            980                 985                 990

Cys His Glu Val Met Ile Thr Ile Asp Gly Glu Glu Gly Ile Pro Val
            995                 1000                1005

Gln Val Asp Gly Glu Ala Trp Ile Gln Arg Pro Gly Leu Ile Lys
        1010                1015                1020

Ile Arg Tyr Lys Asn Ala Ala Gln Met Leu Thr Arg Asp Arg Asp
        1025                1030                1035
```

-continued

```
Phe Glu Asn Ser Met Lys Met Trp Glu Tyr Lys His Thr Glu Ile
    1040            1045            1050

Gln Ala Ala Pro Gln Pro Gln Leu Asp Phe Gln Asp Ser Gln Glu
    1055            1060            1065

Ser Leu Ser Asp Glu Glu Tyr Ala Gln Met Gln His Leu Ala Arg
    1070            1075            1080

Leu Ala Glu Asn Leu Ile Ser Lys Leu Asn Asp Leu Ser Lys Ile
    1085            1090            1095

His Gln His Val Ser Val Leu Met Gly Ser Val Asn Ala Ser Ala
    1100            1105            1110

Asn Ile Leu Asn Asp Ile Phe Tyr Gly Gln Asp Ser Gly Asn Glu
    1115            1120            1125

Met Gly Ala Ala Ser Cys Ile Pro Ile Glu Thr Leu Ser Arg Asn
    1130            1135            1140

Asp Ala Val Asp Val Thr Phe Ser Leu Lys Gly Leu Tyr Asp Asp
    1145            1150            1155

Thr Thr Ala Phe Leu Asp Glu Lys Leu Leu Arg Ser Ala Glu Asp
    1160            1165            1170

Glu Thr Ala Leu Gln Ser Ala Leu Asp Ala Met Asn Lys Glu Phe
    1175            1180            1185

Lys Lys Leu Ser Glu Ile Asp Trp Met Asn Pro Ile Phe Val Pro
    1190            1195            1200

Glu Glu Lys Ser Ser Asp Thr Asp Ser Arg Ser Leu Arg Leu Lys
    1205            1210            1215

Ile Lys Phe Pro Lys Leu Gly Lys Lys Lys Val Glu Glu Glu Arg
    1220            1225            1230

Lys Pro Lys Ser Gly Gln Ser Val Gln Ser Phe Ile Gly Asn Leu
    1235            1240            1245

Trp His Arg Arg His Arg Glu Asp Glu Ala Glu Gly Asp Asp Pro
    1250            1255            1260

Leu Thr Pro Ser Arg Ser Gln Leu
    1265            1270
```

RECOMBINANT DGKK GENE FOR FRAGILE X SYNDROME GENE THERAPY

CROSS-REFERENCE TO RELATED APPLICATION

This application is the U.S. national stage application of International Patent Application No. PCT/EP2017/074387, filed Sep. 26, 2017.

The Sequence Listing for this application is labeled "Seq-List.txt" which was created on Mar. 14, 2019 and is 28 KB. The entire content of the sequence listing is incorporated herein by reference in its entirety.

FIELD OF THE INVENTION

The present invention relates to the field of medicine, in particular of Fragile X syndrome. It provides new treatments of Fragile X syndrome.

BACKGROUND OF THE INVENTION

Fragile X syndrome (FXS) is a genetic condition that causes intellectual disability, behavioral and learning challenges and various physical characteristics. Though Fragile X syndrome occurs in both genders, males (1 in 4,000) are more frequently affected than females (1 in 8,000), and generally with greater severity.

Affected individuals usually have delayed development of speech and language by age 2. Most males with fragile X syndrome have mild to moderate intellectual disability, while about one-third of affected females are intellectually disabled. Children with fragile X syndrome may also have anxiety and hyperactive behavior such as fidgeting or impulsive actions. They may have attention deficit disorder (ADD), which includes an impaired ability to maintain attention and difficulty focusing on specific tasks. About one-third of individuals with fragile X syndrome have features of autism spectrum disorders that affect communication and social interactions. Seizures occur in about 15 percent of males and about 5 percent of females with fragile X syndrome.

Most males and about half of females with fragile X syndrome have characteristic physical features that become more apparent with age. These features include a long and narrow face, large ears, a prominent jaw and forehead, unusually flexible fingers, flat feet, and in males, enlarged testicles (macroorchidism) after puberty.

Fragile X syndrome is caused by an expansion of the CGG trinucleotide repeat affecting the Fragile X mental retardation 1 (FMR1) gene on the X chromosome, resulting in a failure to express the fragile X mental retardation protein (FMRP), which is required for normal neural development.

In the mouse, the lack of FMRP is associated to an excessive translation of hundreds of neuronal proteins, notably including post-synaptic proteins. This local protein synthesis deregulation is proposed to underlie the observed defects of glutamatergic synapse maturation and function, and to affect preferentially the hundreds of mRNA species that were reported to bind to FMRP.

There is currently no treatment that has shown benefit specifically for fragile X syndrome. Current trends in treating the disorder only include medications for symptom-based treatments that aim to minimize the secondary characteristics associated with the disorder like symptoms of attention deficit and hyperactivity, anxiety, and aggression. Supportive management has also been developed to optimize functioning in individuals with fragile X syndrome, including speech therapy, occupational therapy, and individualized educational and behavioral programs.

There is thus still a strong need nowadays for medical science to innovate new and efficacious fragile X syndrome treatments. The present invention seeks to meet these and other needs.

SUMMARY OF THE INVENTION

The inventors have surprisingly discovered that expression of a Dgkk (Diacylglycerol Kinase kappa) nucleic acid truncated for its 5' coding region is able to rescue the dendritic spine abnormalities of hippocampal CA1 pyramidal Fmr1-KO neurons. The inventors have also shown that, in this 5' coding region, two domains are of critical importance, a Proline Rich domain and an EPAPE repeated domain.

Accordingly, in a first aspect, the present invention concerns a nucleic acid coding for a human DGKk protein lacking a functional Proline Rich Region and/or a functional EPAPE repeated Region.

Preferably, this human DGKk protein lacks a functional Proline Rich Region and a functional EPAPE repeated Region.

In particular, the human DGKk protein according to the invention may lack a Proline Rich Region and/or an EPAPE repeated Region.

Preferably, the nucleic acid according to the invention has at least about 85% of identity, preferably at least about 90% of identity, more preferably at least about 95% of identity, with a nucleotide sequence of SEQ ID No: 1 and comprises one or more mutations, preferably deletions, and/or epigenetic modifications in the nucleotide sequences in positions 70-132 and/or 142-539 of SEQ ID No: 1, and optionally one or more mutations, preferably deletions, and/or epigenetic modifications in the nucleotides sequences in positions 4-69, and/or 133-141, and/or 540-648 of SEQ ID No: 1.

More preferably, the nucleic acid according to the invention has at least about 85% of identity, preferably at least about 90% of identity, more preferably at least about 95% of identity, with a nucleotide sequence of SEQ ID No: 1 and comprises a deletion of a sequence selected from the group consisting in sequence in positions 70-132 of SEQ ID No: 1, sequence in positions 142-539 of SEQ ID No: 1, sequences in positions 70-132 and 142-539 of SEQ ID No: 1, sequence in positions 70-539 of SEQ ID No: 1, sequence in positions 4-132 of SEQ ID No: 1, sequence in positions 4-142 of SEQ ID No: 1, sequence in positions 4-539 of SEQ ID No: 1, and sequence in positions 4-648 of SEQ ID No: 1.

Even more preferably, the nucleic acid according to the invention has the sequence of SEQ ID No: 1 and comprises a deletion of a sequence selected from the group consisting in sequence in positions 70-132 of SEQ ID No: 1, sequence in positions 142-539 of SEQ ID No: 1, sequences in positions 70-132 and 142-539 of SEQ ID No: 1, and sequence in positions 4-539 of SEQ ID No: 1.

The invention also concerns, in a second aspect, an expression cassette comprising a nucleic acid according to the invention and a promoter. Preferably, the promoter is a neuron specific promoter, more preferably the human synapsin-1 gene promoter.

The invention also concerns, in a third aspect, an expression vector comprising a nucleic acid according to the invention or an expression cassette according to the invention. Preferably, the expression vector is an adeno-associated virus, more preferably the adeno-associated virus 2/9 or the adeno-associated virus 2/10, even more preferably the adeno-associated virus 2/9.

In a fourth embodiment, the invention concerns a nucleic acid according to the invention, an expression cassette according to the invention, or an expression vector according to the invention, for use as a drug.

The invention also concerns, in a fifth aspect, a pharmaceutical composition comprising a nucleic acid according to the invention, an expression cassette according to the invention, or an expression vector according to the invention.

In a sixth aspect, the invention also concerns a nucleic acid according to the invention, an expression cassette according to the invention, an expression vector according to the invention, or a pharmaceutical composition according to the invention for use in the treatment of fragile X syndrome in a patient in needs thereof.

Preferably, the nucleic acid, expression vector, or pharmaceutical composition is used in combination with a PPAR gamma agonist, preferably a PPAR gamma agonist of the thiazolinedione family, more preferably a molecule selected from the group consisting of pioglitazone, lobeglitazone, ciglitazone, darglitazone, englitazone, netoglitazone, rivoglitazone, and troglitazone, and even more preferably pioglitazone.

The invention also concerns, in an seventh aspect, a kit comprising a nucleic acid according to the invention, an expression cassette according to the invention, an expression vector according to the invention, or a pharmaceutical composition according to the invention and means for the administration of said nucleic acid or said expression cassette or said expression vector or said pharmaceutical composition and optionally a leaflet providing guidelines to use such a kit.

Figure 1:
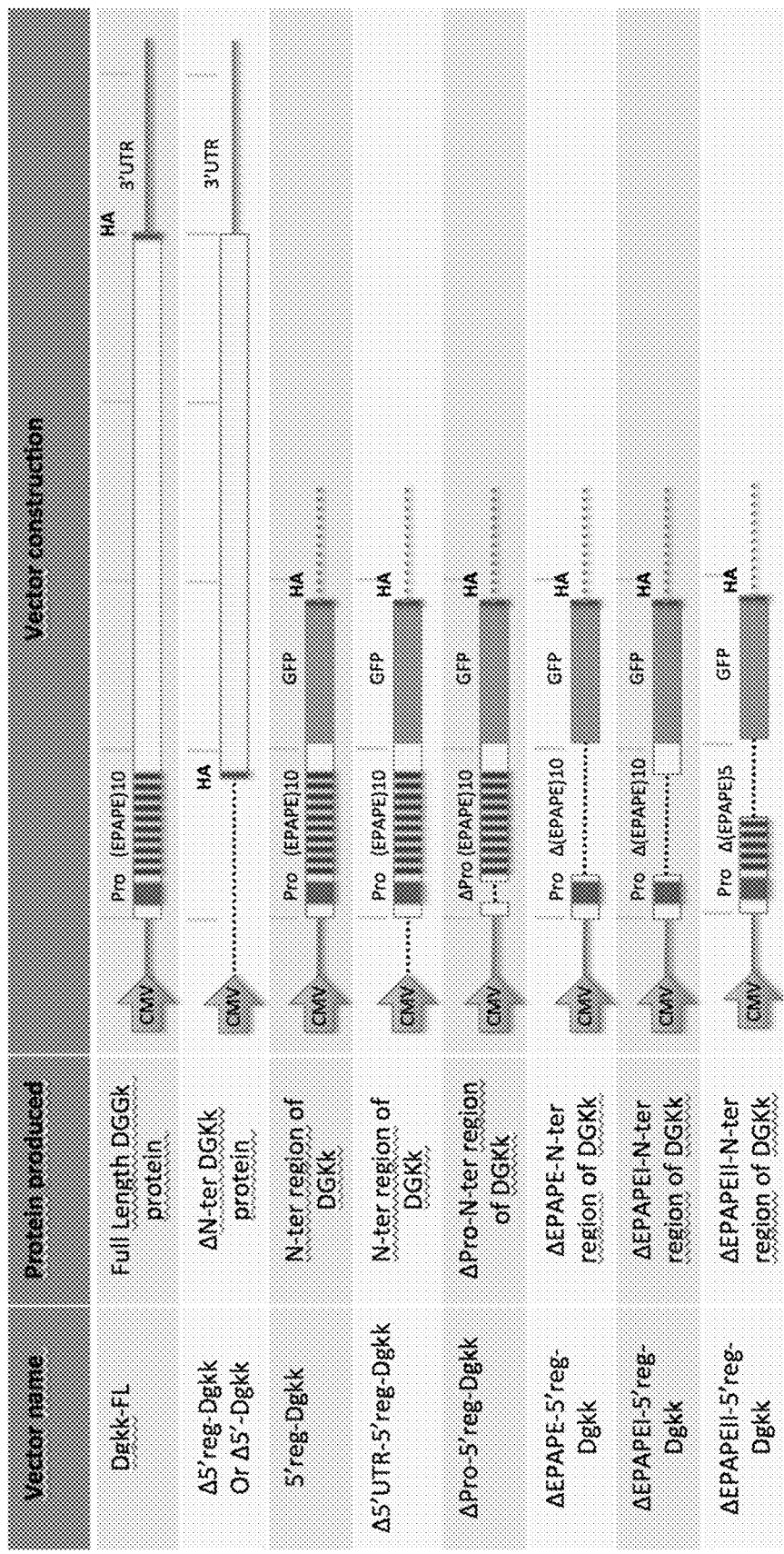
FIG. 1: Map of mouse Dgkk constructions, represented to scale. Two main domains of the 5' coding region of Dgkk are indicated: Pro which refers to the Proline Rich region, and (EPAPE)$_{10}$ which refers to the EPAPE repeated region. HA refers to the hemagglutinin tag, GFP refers to the Green Fluorescent Protein and CMV refers to the Cytomegalovirus promoter. The symbol Δ means that the following DNA or protein region is missing. The term "5' region" refers to the 5' coding region of Dgkk that comprise the Proline Rich region and the EPAPE repeated region and the 5'UTR of Dgkk. The term "N-ter" refers to the protein region corresponding to the 5' coding region of the Dgkk gene. The term "FL" refers to Full Length and the Dgkk-FL vector carries a sequence comprising all the Dgkk exons, its 5'UTR region, its 3'UTR region and a HA tag. The grey bars represent 1 kb.

pathology and support a model where FMRP, by controlling the translation of Dgkk, indirectly controls synaptic proteins translation and membrane properties by impacting lipid signaling in dendritic spine.

The inventors have discovered that, in the absence of FMRP in a cell model, overexpression of a full-length Dgkk nucleic acid does not lead to DGKk protein expression. Accordingly, full-length Dgkk nucleic acid overexpression is unable to rescue the effects of the absence of FMRP. However, they have surprisingly observed that overexpression of a Dgkk truncated for the 5' coding region abolishes the FMRP control and lead to DGKk protein expression. Expression of this truncated Dgkk nucleic acid was shown to be able to rescue the dendritic spine abnormalities of hippocampal CA1 pyramidal Fmr1-KO neurons. The inventors have also shown that in this 5' coding region of Dgkk nucleic acid, two domains were of critical importance: a Proline Rich domain and an EPAPE repeated domain. The absence of a functional Proline Rich domain or of a functional EPAPE repeated domain was indeed sufficient to abolish the FMRP control.

Thus, in a first aspect, the invention relates to a nucleic acid coding for a human DGKk protein lacking a functional Proline Rich Region and/or a functional EPAPE repeated region. Preferably, the nucleic acid coding for a human DGKk protein lacks a functional Proline Rich region and a functional EPAPE repeated region.

Definitions

As used herein, the terms "fragile X Syndrome", "fra(X) syndrome", "FXS", "FRAXA syndrome", "marker X syndrome", "Martin-Bell syndrome", "X-linked mental retardation and macroorchidism" and "Escalante's syndrome" are equivalent and can be used one for the other in the present application. As used herein, "fragile X syndrome" refers to a genetic condition that causes intellectual disabil-

| T.test  | Total | 7-8   | 8-9   | 9-10  | 10-11 | 11-12 | 12-13 | 13-14 | 14-15 | 15-16 | 16-17 | 17-18 | 18-19 | 19-20 | 20-21 |
|---------|-------|-------|-------|-------|-------|-------|-------|-------|-------|-------|-------|-------|-------|-------|-------|
| wt vs A | 0.039 | 0.187 | 0.000 | 0.014 | 0.000 | 0.001 | 0.009 | 0.030 | 0.045 | 0.045 | 0.414 | 0.877 | 0.580 | 0.585 | 0.295 |
| wt vs B | 0.657 | 0.982 | 0.500 | 0.939 | 0.100 | 0.985 | 0.627 | 0.332 | 0.474 | 0.474 | 0.241 | 0.728 | 0.529 | 0.844 | 0.636 |
| wt vs C | 0.564 | 0.771 | 0.097 | 0.279 | 0.444 | 0.444 | 0.967 | 0.858 | 0.741 | 0.741 | 0.427 | 0.371 | 0.651 | 0.623 | 0.373 |

| T.test  | Total | 21-22 | 22-23 | 23-00 | 00-01 | 01-02 | 02-03 | 03-04 | 04-05 | 05-06 | 06-07 |
|---------|-------|-------|-------|-------|-------|-------|-------|-------|-------|-------|-------|
| wt vs A | 0.039 | 0.010 | 0.040 | 0.013 | 0.423 | 0.143 | 0.250 | 0.371 | 0.396 | 0.499 | 0.014 |
| wt vs B | 0.657 | 0.394 | 0.793 | 0.804 | 0.413 | 0.521 | 0.470 | 0.211 | 0.980 | 0.717 | 0.938 |
| wt vs C | 0.564 | 0.521 | 0.418 | 0.348 | 0.892 | 0.903 | 0.607 | 0.919 | 0.887 | 0.738 | 0.461 |

DETAILED DESCRIPTION OF THE INVENTION

Recently, the inventors have shown, in cortical neurons, that FMRP is mostly associated with one unique mRNA: diacylglycerol kinase kappa (Dgkk), a master-regulator that controls the switch between diacylglycerol and phosphatidic acid signaling pathways (cf. Tabet R et al, 2016, Proc Natl Acad Sci USA, pii: 201522631). The absence of FMRP in neurons leads to a loss of Dgkk expression. The inventors have demonstrated that reduction of Dgkk expression in neurons is sufficient to cause dendritic spine abnormalities, synaptic plasticity alterations, and behavior disorders similar to those observed in the fragile X syndrome mouse model. Accordingly, overexpression of Dgkk in neurons is able to rescue the absence of FMRP. Altogether, these data suggest that Dgkk deregulation contributes to fragile X syndrome ity, behavioral and learning challenges and various physical characteristics. Fragile X syndrome is the result of a failure to express the fragile X mental retardation protein.

As used herein, the terms "Intellectual disability (ID)", "general learning disability", or "mental retardation (MR)" are equivalent and can be used one for the other in the present application. As used herein "Intellectual disability" refers to a generalized neurodevelopmental disorder characterized by significantly impaired intellectual and/or adaptive functioning.

As used herein, the terms "fragile X mental retardation protein" or "FMRP" refers to a protein (NCBI Reference Sequence: NP_001172004.1; Uniprot KB: Q06787) coded by the Fragile X mental retardation 1 gene (FMR1, Gene ID: 2332) located on the X chromosome. This protein is required for normal neural development.

In general, Fragile X syndrome occurs as a result of an increase in the number of CGG trinucleotide repeats in the 5' untranslated region of FMR1. Depending on the length of the CGG repeat, an FMR1 allele may be classified as:

normal, between 6 and 54 CGG repeats, the carrier is unaffected by the syndrome;

a premutation, between 55 and about 200 CGG repeats, the carrier is at risk of other FMR-related disorders;

a full mutation, more than about 200 CGG repeats, the carrier is usually affected by the Fragile X syndrome.

Loss of function mutations and/or abnormal gene methylation of FMR1 may also be involved in Fragile X syndrome.

As used herein, the term "diacylglycerol kinase kappa" or "DGKk" refers to a protein (NCBI Reference Sequence: NP_001013764.1; Uniprot KB: Q5KSL6; SEQ ID NO: 9) coded by the Dgkk gene (Gene ID: 139189) located on the X chromosome. DGKk is an enzyme capable to convert Diacylglycerol into Phosphatidic acid.

As used herein, the terms "nucleic acid molecule" or "nucleic acid" refer to an oligonucleotide or a polynucleotide. A nucleic acid molecule may include deoxyribonucleotides, ribonucleotides, modified nucleotides or nucleotide analogs in any combination.

As used herein, the term "nucleotide" refers to a chemical moiety having a sugar (modified, unmodified, or an analog thereof), a nucleotide base (modified, unmodified, or an analog thereof), and a phosphate group (modified, unmodified, or an analog thereof). Nucleotides include deoxyribonucleotides, ribonucleotides, and modified nucleotide analogs including, for example, locked nucleic acids ("LNAs"), peptide nucleic acids ("PNAs"), L-nucleotides, ethylene-bridged nucleic acids ("ENAs"), arabinoside, and nucleotide analogs (including abasic nucleotides).

As used herein, the term "splicing" refers to a modification of a pre-RNA transcript in which introns are removed and exons are joined.

As used herein, the terms "intron" or "intronic sequence" refers to any nucleotide sequence within a gene that is removed by RNA splicing during maturation of the final RNA product. Sequences that are joined together in the final mature RNA after RNA splicing are "exons" or "exonic sequences". The terms "intron" and "exon" refer to both the DNA sequences within a gene and the corresponding sequences in RNA transcripts.

In particular, a nucleic acid according to the invention is preferably a DNA polynucleotide which has been isolated from a naturally occurring gene and/or which has been modified to contain segments of nucleic acids which have been combined or juxtaposed in a manner which would not otherwise exist in nature, preferably by removing the intronic sequences originally present in the naturally occurring gene.

As used herein, the terms "5' UTR", "5' untranslated region", "leader sequence" or "leader RNA" are equivalent and can be used one for the other. They refer to the region of an mRNA that is directly upstream from the initiation codon. This region is important for the regulation of the translation of a transcript. The term "5'UTR" refers to both the DNA sequence within a gene and the corresponding sequences in RNA transcripts.

As used herein, the terms "sequence identity" or "identity" refers to an exact nucleotide to nucleotide correspondence of two polynucleotides. Percent of identity can be determined by a direct comparison of the sequence information between two molecules by aligning the sequences, counting the exact number of matches between the two aligned sequences, dividing by the length of the shorter sequence, and multiplying the result by 100.

The sequence identity can be determined by alignment of two nucleotide sequences using global or local alignment algorithms, depending on the length of the two sequences.

Sequences of similar lengths are preferably aligned using a global alignment algorithms (e.g. Needleman Wunsch) which aligns the sequences optimally over the entire length, while sequences of substantially different lengths are preferably aligned using a local alignment algorithm (e.g. Smith Waterman). Sequences may then be referred to as "substantially identical" or "essentially similar" when they (when optimally aligned by for example the programs GAP or BESTFIT using default parameters) share at least a certain minimal percentage of sequence identity. GAP uses the Needleman and Wunsch global alignment algorithm to align two sequences over their entire length (full length), maximizing the number of matches and minimizing the number of gaps. A global alignment is suitably used to determine sequence identity when the two sequences have similar lengths. Generally, the GAP default parameters are used, with a gap creation penalty=50 (nucleotides) and gap extension penalty=3 (nucleotides). For nucleotides, the default scoring matrix used is nwsgapdna (Henikoff & Henikoff, 1992, PNAS, 89: 915-919). Sequence alignments and scores for percentage sequence identity may be determined using computer programs, such as the GCG Wisconsin Package, Version 10.3, available from Accelrys Inc., 9685 Scranton Road, San Diego, Calif. 92121-3752 USA, or using open source software, such as the program "needle" (using the global Needleman Wunsch algorithm) or "water" (using the local Smith Waterman algorithm) in EmbossWIN version 2.10.0, using the same parameters as for GAP above, or using the default settings (both for "needle" and for "water", the default Gap opening penalty is 10.0 and the default gap extension penalty is 0.5; default scoring matrices are Blossum62 for proteins and DNAFull for DNA). When sequences have a substantially different overall lengths, local alignments, such as those using the Smith Waterman algorithm, are preferred. Alternatively percentage similarity or identity may be determined by searching against public databases, using algorithms such as FASTA, BLAST, etc.

As used herein, the terms "proline rich domain", "proline rich region", "proline rich sequence", "proline rich segment" and "PRR" are equivalent and can be used one for another. They refer to a portion of a protein comprising mostly prolines. The term "proline rich region" refers to both a portion of protein comprising mostly prolines and to the DNA sequence within a gene coding for it. Human DGKk presents an N-terminal proline rich region (corresponding to the nucleotide region between nucleotides 70 and 132 in SEQ ID No: 1).

As used herein, the terms "EPAPE repeated domain", "EPAPE repeated region", "EPAPE repeated sequence", "EPAPE repeated segment" are equivalent and can be used one for another. They refer to a portion of a protein comprising several repetitions of the EPAPE motif, i.e. the succession of Glutamic acid, Proline, Alanine, Proline and Glutamic acid. The term "EPAPE repeated region" refers to both a portion of protein comprising several repetitions of the EPAPE motif and to the DNA sequence within a gene coding for it. Human DGKk presents an N-terminal EPAPE repeated region (corresponding to the nucleotide region between nucleotides 142 and 539 in SEQ ID No: 1).

In the peptide or protein sequences described in this document, amino-acids are represented by their one letter code according to the following nomenclature: A: Alanine; C: cysteine; D: aspartic acid; E: glutamic acid; F: phenylalanine; G: glycine; H: histidine; I: isoleucine; K: lysine; L:

leucine; M: methionine; N: asparagine; P: proline; Q: glutamine; R: arginine; S: serine; T: threonine; V: valine; W: tryptophan and Y: tyrosine.

As used herein, the term "mutation" refers to the alteration of the nucleotide sequence of a gene. The term mutation encompasses, without being limited to them, substitutions, deletions and insertions.

As used herein, the term "substitution" or "point mutation" are equivalent and refers to a mutation consisting in the exchange of a single nucleotide for another. Preferably, the substitution according to the invention is a missense mutation. In a missense mutation, the nucleotide exchanged is part of a triplet of nucleotides that codes, after the mutation, for a different amino acid than the original triplet. Preferably, the mutation is not a silent mutation or a non-sense mutation. In a silent mutation, the nucleotide exchanged is part of a triplet of nucleotides that codes, after the mutation, for the same amino-acid as the original triplet. In a non-sense mutation, the nucleotide exchanged is part of a triplet of nucleotides that codes, after the mutation, for a stop codon and can thus truncates the protein.

As used herein, the term "deletion" refers to a mutation consisting in the removal of one or more nucleotides from the DNA. Deletions according to the invention do not lead to a shift in the reading frame (frameshift). Therefore the number of deleted nucleotides is a multiple of three.

As used herein, the term "insertion" refers to a mutation consisting in the addition of one or more extra nucleotides into the DNA. Insertions according to the invention do not lead to a shift in the reading frame. Therefore the number of inserted nucleotides is a multiple of three.

As used herein, the term "epigenetic modification" refers to functionally relevant changes to the genome that do not involve a change in the nucleotide sequence. Examples of mechanisms that produce such changes are DNA methylations and histone modifications.

As used herein, the term "expression cassette" refers to a nucleic acid construction comprising a coding region and regulatory regions necessary for expression, operably linked to the coding region. The expression "operably linked" indicates that the elements are combined in such a way that the expression of the coding region is under the control of the regulatory regions. Typically, a regulatory region is located upstream of the coding region at a distance compatible with the control of its expression. The regulatory region can include promoters, enhancers, silencers, attenuators, and internal ribosome entry sites (IRES). Spacer sequences may also be present between regulatory elements and the coding region, as long as they don't prevent its expression. An expression cassette may also include a start codon in front of a protein-encoding gene, splicing signals for introns, and stop codons, transcription terminators, polyadenylation sequences.

As used herein, the terms "promoter" and "transcriptional promoter" are equivalent and refer to a region of DNA that is part of the regulatory region of an expression cassette. The promoter is the regulatory element that initiates the transcription of a particular gene. Promoters are located near the transcription start site of genes, on the same strand and upstream on the DNA (towards the 5' region of the sense strand). As used herein, the term "constitutive promoter" refers to a promoter that is active in most tissues and in most circumstances in the cell. The terms "regulated promoter" or "inducible promoter", as used herein, are equivalent and refers to promoters that are activated or repressed in the cells only in response to specific physical or chemical stimuli. The term "specific promoter" refers to promoters that can only be activated in a specific organ or tissue, such as the brain, or in a specific cell-type, such as neurons.

As used herein, the term "enhancer" refers to a short (50-1500 bp) region of DNA that is part of the regulatory region. An enhancer is a regulatory element that can be bound by proteins (activators) to increase the likelihood that transcription will occur at a gene. Enhancers are generally cis-acting, located up to 1 Mbp (1,000,000 bp) away from the gene and can be upstream or downstream from the start site, and either in the forward or backward direction.

As used herein, the term "transcription terminator" refers to a section of nucleic acid sequence that can be part of an expression cassette and that marks the end of a gene during transcription. This sequence mediates transcriptional termination by providing signals in the newly synthesized mRNA that trigger processes which release the mRNA from the transcriptional complex.

As used herein, the term "vector" refers to a nucleic acid molecule, typically DNA or RNA that serves to transfer a passenger nucleic acid sequence, i.e. DNA or RNA, into a host cell. A vector may comprise an origin of replication, a selectable marker, and a suitable site for the insertion of a gene such as the multiple cloning site. There are several common types of vectors including plasmids, phages, phagemids, viruses, cosmids, and artificial chromosomes. Preferably, the vector of the invention is a DNA viral vector.

A "viral vector", as used herein, refers to a vector comprising some or all of the following: viral genes encoding a gene product, control sequences and viral packaging sequences.

A "parvoviral vector", as used herein, refers to a recombinantly produced parvovirus or parvoviral particle that comprises a polynucleotide to be delivered into a host cell, either in vivo, ex vivo or in vitro. Examples of parvoviral vectors include e.g., adeno-associated virus vectors (AAV), for example AAV1, AAV2, AAV3, AAV4, AAV5, AAV6, AAV7, AAV8, AAV9, AAV10 and AAV-PHP.B (Devernam et al, 2016, Nature Biotechnology, 34, 204-206). Herein, a parvoviral vector also refers to the polynucleotide comprising the viral genome or part thereof, and a nucleic acid of interest. In particular, modified AAV sequences can also be used in the context of the present invention. Such modified sequences include AAVs where parts of other AAV can be used in place of wild-type AAV ITR (interverted terminal repeats), Rep (Replication protein), or VP (viral protein) sequences. The AAV VP proteins are known to determine the cellular tropicity of the AAV virion. The VP protein-encoding sequences are significantly less conserved than ITR and Rep proteins and genes among different AAV serotypes. The ability of Rep and ITR sequences to cross-complement corresponding sequences of other serotypes allows for the production of pseudotyped AAV particles comprising the capsid proteins of one serotype (e.g., AAV5) and the ITR sequences of another AAV serotype (e.g., AAV2). Such pseudotyped AAV particles may be referred to as being of the type "x/y", where "x" indicates the source of ITR sequences and "y" indicates the serotype of the capsid, for example an AAV 2/9 particle has ITR sequences from AAV2 and a capsid from AAV5.

As used herein, the term "expression vector" refers to a vector designed for gene expression in cells. An expression vector allows to introduce a specific gene into a target cell, and can commandeer the cell's mechanism for protein synthesis to produce the protein encoded by the gene. An expression vector comprises expression elements including, for example, a promoter, the correct translation initiation sequence such as a ribosomal binding site and a start codon, a termination codon, and a transcription termination sequence. An expression vector may also comprise other regulatory regions such as enhancers, silencers and boundary elements/insulators to direct the level of transcription of a given gene. The expression vector can be a vector for stable or transient expression of a gene. As used herein, "stable expression" refers to a gene expression which is sustained in time, even after host cells replicate. For a stable expression, the introduced genetic material has to be integrated into the host genome. An integrative expression vector is an expression vector suitable for stable expression. As used herein "transient expression" refers to a gene expression which is limited in time, preferably between 1 day and 1 year, more preferably between 10 days and 8 months, still preferably between 1 month and 6 months, and even more preferably between 2 months and 4 months. For a transient gene expression, the introduced genetic material has to not be integrated into the host genome.

As used herein, the term "treatment", "treat" or "treating" refers to any act intended to ameliorate the health status of patients, such as therapy and prevention of the disease.

As used herein, the term "effective amount" refers to a quantity of a nucleic acid, expression cassette, expression vector or pharmaceutical composition which prevents, delays, removes or reduces the deleterious effects of fragile X syndrome.

As used herein, the terms "active principle", "active ingredient" and "active pharmaceutical ingredient" are equivalent and refers to a component of a pharmaceutical composition having a therapeutic effect.

As used herein, the term "therapeutic effect" refers to an effect induced by an active ingredient or by a pharmaceutical composition according to the invention, capable to prevent or to delay the appearance of fragile X syndrome, or to cure or to attenuate the effects of fragile X syndrome.

As used herein, the term "excipient or pharmaceutically acceptable carrier" refers to any ingredient except active ingredients that is present in a pharmaceutical composition. Its addition may be aimed to confer a particular consistency or other physical or gustative properties to the final product. An excipient or pharmaceutically acceptable carrier must be devoid of any interaction, in particular chemical, with the actives ingredients.

As used herein, the term "gene therapy" refers to a technique that uses genes to treat, attenuate, delay or prevent diseases, such as fragile X syndrome. In particular, gene therapy can be a gene augmentation therapy and may refer to the introduction of a modified human Dgkk gene into the body to help fighting fragile X syndrome. Alternatively, gene therapy can be a deletion gene therapy and may refer to the deletion of parts of human Dgkk into the genome of cells to help fighting fragile X syndrome.

As used herein, the terms "subject", "individual" or "patient" are interchangeable and refer to an animal, preferably to a mammal, even more preferably to a human, including adult, child, new-borns and human at the prenatal stage.

As used herein, the terms "molecules of the thiazolidinedione family", "thiazolidinediones" or "glitazones" are interchangeable and refer to a class of molecules that contain a functional group in which thiazolidine serves as a dione. Thiazolidinediones are able to bind the nuclear PPAR-Gamma receptor (Peroxisome proliferator-activated receptor gamma). The thiazolidinedione according to the invention may be selected from the group constituted of pioglitazone, lobeglitazone, ciglitazone, darglitazone, englitazone, netoglitazone, rivoglitazone, and troglitazone. Preferably, the thiazolidinedione according to the invention is pioglitazone.

As used herein the term "mGluR" and "metabotropic glutamate receptor" are interchangeable and refer to members of the group C family of G-protein-coupled receptors that can bind glutamate. mGluRs are active through an indirect metabotropic process. The mGluR ligand according to the invention may be any molecule capable to bind mGluRs. The mGluR ligand according to the invention may be an agonist of the mGluR.

In the present document, the term «about» refers to a range of values of ±10% of the specified value. For example, «about 50» comprise values of ±10% of 50, i.e. values in the range between 45 and 55. Preferably, the term «about» refers to a range of values of ±5% of the specified value.

Nucleic Acid

The invention refers to a nucleic acid coding for a human DGKk protein. The nucleic acid according to the invention lacks a functional Proline Rich region and/or a functional EPAPE repeated region. A "functional region" or a "functional domain", as used herein, are equivalent and refer to a region involved in the control of the expression of the human Dgkk gene by FMRP. The absence of a functional Proline Rich region or of a functional EPAPE repeated region in a human Dgkk gene abolishes or reduces the FMRP control on the expression of this gene. The absence of a functional Proline Rich region or of a functional EPAPE repeated region in a human Dgkk gene allows the expression of this Dgkk gene independently of FMRP. The nucleic acid according to the invention may lack a functional Proline Rich region and/or a functional EPAPE repeated region because one or both of these regions are non-functional or have been deleted.

In a particular embodiment, the nucleic acid according to the invention codes for a human DGKk protein comprising a non-functional Proline Rich region and/or a non-functional EPAPE repeated region.

In another particular embodiment, the nucleic acid according to the invention codes for a protein lacking a Proline Rich region and/or an EPAPE repeated region. In particular, the Proline Rich region and/or an EPAPE repeated region has been deleted.

In some embodiment, the nucleic acid according to the invention codes for a human DGKk protein which expression is independent of FMRP.

Preferably, the nucleic acid according to the invention comprises one or several mutations in its sequence, resulting into a nucleic acid lacking a functional Proline rich region and/or a functional EPAPE repeated region. The mutations according to the invention may be substitutions, deletions and/or insertions. The mutations may be in or within the concerned regions. Alternatively, the nucleic acid according to the invention comprises one or several epigenetic modifications resulting into a nucleic acid lacking a functional Proline rich region and/or a functional EPAPE repeated region.

In a particular embodiment, the nucleic acid according to the invention comprises a deletion of at least 10%, 20%, 30%, 40%, 50%, 60%, 70%, 80%, 90%, 95%, 99% of the Proline rich region and/or a the EPAPE repeated region.

The nucleic acid according to the invention codes for a functional "DGKk protein". As used herein, the term "functional protein" refers to a human DGKk protein which is capable to fulfill the same functions in a cell than a normal DGKk protein. Preferably, it is subjected to the same regulations as a normal DGKk protein except that the regulation of its expression by FMRP is abolished. In particular, the catalytic function of the DGKk protein is conserved in the protein coded by the nucleic acid according to the invention. In particular, the catalytic function is the capacity to phosphorylate diacylglycerol (DAG) to generate phosphatidic acid (PA). In particular, a functional DGKk protein comprises a Pleckstrin homology domain (PH domain) and a catalytic domain. The PH domain is between positions 216 and 309 and the catalytic domain is between positions 487 and 622 of the human DGKk protein (as disclosed in NCBI Reference Sequence: NP_001013764.1; Uniprot KB: Q5KSL6; see also SEQ ID NO: 9).

Preferably, the nucleic acid according to the invention comprises only exonic sequences.

Preferably, the nucleic acid according to the invention is devoid of 5'UTR.

In a particular embodiment, the nucleic acid according to the invention codes for a human DGKk protein lacking a functional Proline Rich region. Preferably, the nucleic acid according to the invention codes for a human DGKk protein lacking a Proline Rich region. Alternatively, the nucleic acid according to the invention codes for a human DGKk protein comprising a non-functional Proline Rich region.

In a preferred embodiment, the nucleic acid according to the invention codes for a human DGKk protein lacking a functional EPAPE repeated region. Preferably, the nucleic acid according to the invention codes for a human DGKk protein lacking an EPAPE repeated region. Alternatively, the nucleic acid according to the invention codes for a human DGKk protein comprising a non-functional EPAPE repeated region.

In a more preferred embodiment, the nucleic acid according to the invention codes for a human DGKk protein lacking a functional Proline Rich region and a functional EPAPE repeated region. Preferably, the nucleic acid according to the invention codes for a human DGKk protein lacking a Proline Rich region and an EPAPE repeated region. Alternatively, the nucleic acid according to the invention codes for a human DGKk protein comprising a non-functional Proline Rich region and a non-functional EPAPE repeated region.

In a preferred embodiment, the nucleic acid according to the invention lacks a functional Proline Rich region and/or a functional EPAPE repeated region because of mutations, preferably deletions, and/or epigenetic modifications in its sequence. Accordingly, the nucleic acid according to the invention can be a nucleic acid having at least about 70% of identity, preferably at least about 80% of identity, more preferably at least about 90% of identity, still preferably at least about 95% of identity, and even more preferably at least about 99% of identity, with a nucleotide sequence of SEQ ID No: 1 and comprises one or several mutations, preferably deletions, and/or epigenetic modifications in the nucleotide sequences in positions 70-132 and/or 142-539 of SEQ ID No: 1, and optionally one or several mutations, preferably deletions, and/or epigenetic modifications in the nucleotides sequences in positions 4-69, and/or 133-141, and/or 540-648 of SEQ ID No: 1.

In another particular embodiment the nucleic acid according to the invention is a nucleic acid having at least about 70% of identity, preferably at least about 80% of identity, more preferably at least about 90% of identity, still preferably at least about 95% of identity, and even more preferably at least about 99% of identity, with a nucleotide sequence of SEQ ID No: 1 and comprises one or several mutations, preferably deletions, and/or epigenetic modifications in the nucleotide sequences in positions 70-132 and/or 142-539 of SEQ ID No: 1.

In yet another particular embodiment the nucleic acid according to the invention is a nucleic acid having at least about 70% of identity, preferably at least about 80% of identity, more preferably at least about 90% of identity, still preferably at least about 95% of identity, and even more preferably at least about 99% of identity, with a nucleotide sequence of SEQ ID No: 1 and comprises one or several mutations, preferably deletions, and/or epigenetic modifications in the nucleotide sequence in positions 70-132 of SEQ ID No: 1.

In still another particular embodiment the nucleic acid according to the invention is a nucleic acid having at least about 70% of identity, preferably at least about 80% of identity, more preferably at least about 90% of identity, still preferably at least about 95% of identity, and even more preferably at least about 99% of identity, with a nucleotide sequence of SEQ ID No: 1 and comprises one or several mutations, preferably deletions, and/or epigenetic modifications in the nucleotide sequences in positions 142-539 of SEQ ID No: 1.

In a preferred particular embodiment the nucleic acid according to the invention is a nucleic acid having at least about 70% of identity, preferably at least about 80% of identity, more preferably at least about 90% of identity, still preferably at least about 95% of identity, and even more preferably at least about 99% of identity, with a nucleotide sequence of SEQ ID No: 1 and comprises one or several mutations, preferably deletions, and/or epigenetic modifications in the nucleotide sequences in positions 70-132 and 142-539 of SEQ ID No: 1.

Preferably, when mutations are deletions, the total deletion rate in sequence 70-132 and/or in sequence 142-539 is of at least about 20%, preferably at least about 30%, more preferably of at least about 40%, still more preferably of at least about 50%, 60%, 70%, 75%, 80%, 85%, 90%, 95%, and even more preferably at least about 99% of the corresponding nucleotide sequence.

In another particular embodiment the nucleic acid according to the invention is a nucleic acid having at least about 70% of identity, preferably at least about 80% of identity, more preferably at least about 90% of identity, still preferably at least about 95% of identity, and even more preferably at least about 99% of identity, with a nucleotide sequence of SEQ ID No: 1 and comprises the deletion of nucleotides 70-132 and/or 142-539 of SEQ ID No: 1, and optionally one or several deletions in the nucleotide sequences in positions 4-69, and/or 133-141, and/or 540-648 of SEQ ID No: 1.

In a preferred embodiment, the nucleic acid according to the invention is a nucleic acid having at least about 70% of identity, preferably at least about 80% of identity, more preferably at least about 90% of identity, still preferably at least about 95% of identity, and even more preferably at least about 99% of identity, with a nucleotide sequence of SEQ ID No: 1 and comprises a deletion of a sequence selected from the group consisting in sequence in positions 70-132 of SEQ ID No: 1, sequence in positions 142-539 of SEQ ID No: 1, sequences in positions 70-132 and 142-539 of SEQ ID No: 1, sequence in positions 70-539 of SEQ ID No: 1, sequence in positions 4-132 of SEQ ID No: 1, sequence in positions 4-142 of SEQ ID No: 1, sequence in positions 4-539 of SEQ ID No: 1, and sequence in positions 4-648 of SEQ ID No: 1.

In a more preferred embodiment, the nucleic acid according to the invention is a nucleic acid having at least about 70% of identity, preferably at least about 80% of identity, more preferably at least about 90% of identity, still preferably at least about 95% of identity, and even more preferably at least about 99% of identity, with a nucleotide sequence of SEQ ID No: 1 and comprises a deletion of a sequence selected from the group consisting in sequence in positions 70-132 of SEQ ID No: 1, sequence in positions 142-539 of SEQ ID No: 1, sequence in positions 70-132 and 142-539 of SEQ ID No: 1, and sequence in positions 4-539 of SEQ ID No: 1.

In an even more preferred embodiment, the nucleic acid according to the invention is a nucleic acid having the sequence of SEQ ID No: 1 and comprises a deletion of a sequence selected from the group consisting in sequence in positions 70-132 of SEQ ID No: 1, sequence in positions 142-539 of SEQ ID No: 1, sequences in positions 70-132 and 142-539 of SEQ ID No: 1, sequence in positions 70-539 of SEQ ID No: 1, sequence in positions 4-132 of SEQ ID No: 1, sequence in positions 4-142 of SEQ ID No: 1, sequence in positions 4-539 of SEQ ID No: 1, and sequence in positions 4-648 of SEQ ID No: 1.

In a particular embodiment, the nucleic acid according to the invention has the sequence of SEQ ID No: 1 in which nucleotides in positions 70-132 have been deleted.

In another particular embodiment, the nucleic acid according to the invention has the sequence of SEQ ID No: 1 in which nucleotides in positions 142-539 have been deleted.

In yet another particular embodiment, the nucleic acid according to the invention has the sequence of SEQ ID No: 1 in which nucleotides in positions 70-132 and 142-539 have been deleted.

In still another particular embodiment, the nucleic acid according to the invention has the sequence of SEQ ID No: 1 in which nucleotides in positions 4-539 have been deleted.

In another particular embodiment, the nucleic acid according to the invention has at least about 70%, 80%, 85%, 90%, 95%, 99%, of identity with the nucleotide sequence in positions 648-3816, preferably 539-3816, more preferably 4-69 and 539-3816, and even more preferably in positions 4-69, 133-141 and 539-3816, of SEQ ID No: 1.

Expression Cassette

The invention also concerns, in a second aspect, an expression cassette comprising a nucleic acid according to the invention operably linked to a regulatory region.

Preferably, the regulatory region of the expression cassette comprises a promoter that allows the expression of the nucleic acid in the host cell, even more preferably, the regulatory region is a promoter. The regulatory region may also comprise other regulatory elements, preferably, the regulatory region comprises at least one enhancer operably linked to the promoter. Spacer sequences may also be present in the expression cassette between the regulatory elements and between the regulatory region and the nucleic acid.

A large variety of promoters suitable for the expression in cells or organisms of the nucleic acid according to the invention can easily be selected by the man skilled in the art. Examples of suitable promoters for use in mammalian cells are e.g. described in Sambrook and Russell (2001) "Molecular Cloning: A Laboratory Manual (3 edition), Cold Spring Harbor Laboratory, Cold Spring Harbor Laboratory Press, New York.

The promoter may be the promoter natively associated with the Dgkk gene.

The promoter may also be a constitutive or an inducible promoter heterologous to the Dgkk gene. Preferably, the promoter is a constitutive promoter.

The promoter according to the invention may also be organ or tissue specific, preferably brain specific. Preferably, the promoter according to the invention is cell-type specific, preferably neurons specific.

Examples of promoter suitable according to the present invention comprise, without limitation, the human synapsin-1 gene promoter, the human calcium/calmodulin-dependent protein kinase II gene promoter, the neuropeptide somatostatin (SST) gene promoter, the human tubulin alpha I gene promoter, the human neuron-specific enolase (NSE) gene promoter, the human platelet-derived growth factor beta chain gene promoter, the human preproenkephalin gene promoter, the human dopamine b hydroxylase (dbH) gene promoter, the human prolactin gene promoter, the human Glial fibrillary acidic protein (GFAP) gene promoter, the human glutamic acid decarboxylase (GAD67) gene promoter, the human homeobox Dlx5/6 gene promoter, the human glutamate receptor 1 (GluR1) gene promoter, the human preprotachykinin 1 (Tac1) gene promoter, the human dopaminergic receptor 1 (Drd1a) gene promoter, the human aromatic L-amino acid decarboxylase (AADC) gene promoter, the neurofilament gene promoter, a fragment of methyl CpG-binding protein 2 (MeCP2) gene promoter (in particular the −677/+56 fragment thereof, as disclosed in Adachi et al, Hum Mol Genet. 2005 14, 3709-22), and the serotonin receptor gene promoter.

Preferably, the promoter according to the invention is the human synapsin-1 gene promoter.

The expression cassette may further comprise a transcription terminator, optionally followed by a 3' inverted terminal repeat (3'ITR), operably linked to the nucleic acid according to the invention. A transcription terminator can easily be chosen by the man skilled in the art. For instance, a suitable transcription terminator is the β-globin transcription terminator or the human growth hormone polyadenylation signal.

Expression Vector

The invention also concerns, in a third aspect, an expression vector comprising a nucleic acid according to the invention or an expression cassette according to the invention.

Preferably, the expression vector is a DNA viral expression vector.

Preferably, the expression vector is suitable for the transformation of mammal cells, preferably human cells.

Expression vectors may be built by classical molecular biology techniques, well known by the man skilled in the art.

Preferably, the expression vector of the invention comprises regulatory elements such as promoters and/or enhancers, preferably a promoter, in particular the human synapsin-1 gene promoter. The methods for selecting these elements according to the host cell in which expression is desired are well known from the man skilled in the art.

The expression vector according to the invention may be a vector for stable or transient expression.

In a particular embodiment, the expression vector is an integrative vector suitable for stable expression. Such a vector comprises one or several sequences allowing the targeted insertion of the expression vector, of the expression cassette, or of the nucleic acid, in the genome of a host cell.

In a preferred embodiment, the expression vector is a vector for transient expression.

Preferably, the expression vector is a vector targeting specifically brain cells. Even more preferably, the expression vector is a vector targeting specifically neurons.

In a preferred embodiment, the expression vector according to the invention is selected from the group consisting in Lentiviral vectors, Herpes simplex virus (HSV), recombinant HSV vectors and parvoviral vector, preferably parvoviral vectors, even more preferably adeno-associated virus vector (AAV).

In an even more preferred embodiment, the expression vector according to the invention is an adeno-associated virus vectors selected from the group consisting in the adeno-associated virus 1, the adeno-associated virus 2, the adeno-associated virus 5, the adeno-associated virus 9, the adeno-associated virus rh.10, the adeno-associated virus 2/1, the adeno-associated virus 2/5, the adeno-associated virus 2/9, the adeno-associated virus 2/rh.10, preferably the expression vector according to the invention is the adeno-associated virus 2/9 or the adeno-associated virus 2/rh.10, even more preferably the adeno-associated virus 2/9.

In a particularly preferred embodiment, the expression vector according to the invention is an adeno-associated virus 2/9 or an adeno-associated virus 2/rh.10 comprising the human synapsin-1 gene promoter, preferably an adeno-associated virus 2/9 comprising the human synapsin-1 gene promoter.

In a particular embodiment, the expression vector according to the invention is an adeno-associated virus vector in which between 1 and about 50 alanines, preferably between about 5 and about 25 alanines, more preferably between about 10 and about 20 alanines, even more preferably 19 alanines, have been added to a VP capsid protein, preferably the VP2 capsid protein. For example, such a vector may be the AAV-AS vector (Choudhury et al, 2016, Mol Ther. 2016, 24, 726-35).

In another particular embodiment, the expression vector according to the invention target specifically glutamatergic neurons. Preferably, such a vector is a vector modified to express an mGluR ligand into its capsid. The mGluR ligand according to the invention may be a mGluR agonist.

Alternatively, peptides mimicking binding domains for cytoplasmic dynein and/or peptides derived from an NMDA receptor antagonist can be inserted in the capsid (Xu et al, 2005, Virology, 341, 203-214).

Use as a Drug

In a fourth aspect, the invention also concerns a nucleic acid according to the invention, an expression cassette according to the invention, or an expression vector according to the invention for its use as a drug.

The invention also concerns a pharmaceutical composition comprising a nucleic acid according to the invention, an expression cassette according to the invention, or an expression vector according to the invention.

The pharmaceutical composition according to the invention may also comprise another active ingredient. In particular, the pharmaceutical composition according to the invention may further comprise a PPAR gamma agonist, preferably a PPAR gamma agonist of the thiazolinedione family, more preferably a molecule selected from the group consisting of pioglitazone, lobeglitazone, ciglitazone, darglitazone, englitazone, netoglitazone, rivoglitazone, and troglitazone, and even more preferably pioglitazone. Indeed, the PPAR gamma agonists, in particular the pioglitazone, have been shown by the inventors to increase or improve the DgK activity. Guidance on co-administration of additional therapeutics may for example be found in the Compendium of Pharmaceutical and Specialties (CPS) of the Canadian Pharmacists Association.

Preferably, the pharmaceutical composition also comprises at least one excipient or pharmaceutically acceptable carrier, preferably selected from the group consisting in solvents, isotonic and absorption delaying agents, antiadherents, binders, coatings, colours, disintegrants, flavors, glidants, lubricants, preservatives, sorbents, sweeteners, and vehicles.

In a preferred embodiment, the invention concerns a nucleic acid according to the invention, an expression cassette according to the invention, an expression vector according to the invention, or a pharmaceutical composition according to the invention, for its use in the treatment of fragile X syndrome or in the treatment of another intellectual disability associated with a decrease in Dgkk expression in neurons, preferably in the treatment of fragile X syndrome, in a subject in need thereof. Optionally, it can be used in combination with another active ingredient. In one embodiment, the other active ingredient is a PPAR gamma agonist, preferably a PPAR gamma agonist of the thiazolinedione family, more preferably a molecule selected from the group consisting of pioglitazone, lobeglitazone, ciglitazone, darglitazone, englitazone, netoglitazone, rivoglitazone, and troglitazone, and even more preferably pioglitazone.

The invention also concerns a method of treatment of fragile X syndrome or another intellectual disability associated with a decrease in Dgkk expression in neurons, preferably fragile X syndrome, in a subject in need thereof comprising the administration of an effective amount of a nucleic acid according to the invention, of an expression cassette according to the invention, of an expression vector according to the invention, or of a pharmaceutical composition according to the invention to the subject. Optionally, the method may further comprise the administration of another active ingredient. In one embodiment, the other active ingredient is a PPAR gamma agonist, preferably a PPAR gamma agonist of the thiazolinedione family, more preferably a molecule selected from the group consisting of pioglitazone, lobeglitazone, ciglitazone, darglitazone, englitazone, netoglitazone, rivoglitazone, and troglitazone, and even more preferably pioglitazone.

The invention also concerns the use of a nucleic acid according to the invention, of an expression cassette according to the invention, of an expression vector according to the invention, in the manufacture of a drug for the treatment of fragile X syndrome or another intellectual disability associated with a decrease in Dgkk expression in neurons, preferably fragile X syndrome, in a subject in need thereof. Optionally, it can be used in combination with another active ingredient. In one embodiment, the other active ingredient is a PPAR gamma agonist, preferably a PPAR gamma agonist of the thiazolinedione family, more preferably a molecule selected from the group consisting of pioglitazone, lobeglitazone, ciglitazone, darglitazone, englitazone, netoglitazone, rivoglitazone, and troglitazone, and even more preferably pioglitazone.

Subject, Regimen and Administration

The subject of the invention is a human, preferably a new-born or a child. Alternatively, the subject can be an adult human.

In a preferred embodiment, the subject has been diagnosed with fragile X syndrome. Diagnostic method of fragile X syndrome is well known by the man skilled in the art. In particular, identification of a loss-of-function mutation in the FMR1 gene is sufficient to diagnose fragile X syndrome in an individual exhibiting developmental delay or intellectual disability. The diagnosis of fragile X syndrome can be summarize in three steps: 1) History and evaluation of development, behavior, and cognitive function; 2) Targeted family history for features of the condition and related FMR1 disorders; 3) Molecular genetic testing, i.e. targeted mutation analysis of the trinucleotide repeat region of FMR, by southern blot or PCR (polymerase chain reaction).

In an alternative embodiment, the subject has not been diagnosed with fragile X syndrome but present another intellectual disability associated with a decrease in Dgkk expression, preferably in neurons. This decrease in Dgkk expression may be the consequence of mutations in the Proline Rich Region and/or in the EPAPE rich region of the Dgkk gene.

Preferably, the treatment of the subject starts less than one year after the diagnosis, preferably less than one month after the diagnosis.

The nucleic acid according to the invention, the expression cassette according to the invention, the expression vector according to the invention, or the pharmaceutical composition according to the invention may be administered by any conventional route of administration, preferably parenteraly, even more preferably by intravenous route of administration. In a particular embodiment, the route of administration is intracranial, for example in the cortex or in the hippocampus areas. The route of administration may also be intrathecal, i.e. administration within the cerebrospinal fluid at any level of the cerebrospinal axis, including injection into the cerebral ventricles (see also "Route of Administration". 25 Data Standards Manual. Food and Drug Administration. Retrieved 11 Mar. 2011).

In a preferred embodiment, the subject is treated by a pharmaceutical composition comprising a transient expression vector. Thus, the treatment has to be administered regularly, preferably between about each week to about a year, more preferably between about 2 weeks and between about 9 months, still preferably between about each month and about each 6 months, even more preferably between about each 2 months and about each 4 months.

Preferably, the expression vector according to the invention is administered at a dose comprised between $10^{10}$ and $10^{13}$, preferably between $10^{11}$ and $10^{12}$, vector genome (VG) per injection. The dose of vector to be administered can be adjusted by the man skilled in the art according to the type of vector, to the patient, in particular its age, weight and general physical condition, and to the severity of the disease.

In a particularly preferred embodiment, the subject is treated by a pharmaceutical composition comprising an adeno-associated virus 2/9 or an adeno-associated virus 2/rh.10 comprising the human synapsin-1 gene promoter operably linked to a nucleic acid of the invention.

Kit and Use of a Kit

The invention also concerns, in a fifth aspect, a kit for the treatment of fragile X syndrome in a subject, wherein the kit comprises a nucleic acid according to the invention, an expression cassette according to the invention, an expression vector according to the invention, or a pharmaceutical composition according to the invention, and means for their administration and optionally a leaflet providing guidelines to use such a kit.

In an additional embodiment, the invention also concerns a kit comprising a nucleic acid according to the invention, an expression cassette according to the invention, an expression vector according to the invention, or a pharmaceutical composition according to the invention and a PPAR gamma agonist of the thiazolinedione family, more preferably a molecule selected from the group consisting of pioglitazone, lobeglitazone, ciglitazone, darglitazone, englitazone, netoglitazone, rivoglitazone, and troglitazone, and even more preferably pioglitazone, as a combined preparation for simultaneous, separate or sequential use, for its use in the treatment of fragile X syndrome or another intellectual disability associated with a decrease in Dgkk expression in neurons, preferably fragile X syndrome, in a subject in need thereof.

The invention also concerns the use of a kit as described above in the treatment of fragile X syndrome or another intellectual disability associated with a decrease in Dgkk expression in neurons, preferably fragile X syndrome, in a subject in need thereof.

Preferably, the subject is a human.

Deletion Gene Therapy

In a sixth aspect, the invention also concerns means for the targeted recombination of the human Dgkk gene in the genome of cells, wherein the resulting recombined Dgkk gene is lacking a functional Proline Rich Region and/or a functional EPAPE repeated Region. The modification or deletion in the Proline Rich region and/or in the EPAPE repeated Region may be introduced by homologous recombination. For instance, the system Crispr/Cas9 can be used to modify the gene.

In a preferred embodiment, the means for the targeted recombination of the human Dgkk gene comprise a nucleic acid coding for guide RNAs specific of this gene. As used herein, the term "guide RNA" refers to a RNA comprising a RNA structure of fixation to the Crispr/Cas9 enzyme and a RNA sequence complementary to the targeted sequence of the Dgkk gene. As used herein, the term "Crisp/Cas9 enzyme" refers to an RNA-guided DNA endonuclease that cleaves the DNA substrate complementary to its guide RNA, and thus allows the recombination of the human Dgkk gene.

Preferably, the guide RNAs are targeting one or several nucleotide sequences comprised in the sequences in positions 70-132 and/or 142-539 of SEQ ID No: 1.

Preferably, means for the targeted recombination of the human Dgkk gene further comprise a nucleic acid coding for the Crispr/Cas9 enzyme. Preferably, the same nucleic acid is coding for the guide RNAs and for the Crispr/Cas9 enzyme.

In a preferred embodiment, the invention consist in an expression vector comprising a promoter operably linked to the gene coding for the Crispr/Cas9 enzyme and the genes coding for guide RNAs which specifically target the recombination of the human Dgkk gene, wherein the resulting recombined Dgkk gene lacks a functional Proline Rich Region and/or a functional EPAPE repeated Region.

Preferably, the expression vector is the adeno-associated virus 2/9 or the adeno-associated virus 2/rh.10, even more preferably the adeno-associated virus 2/9.

Preferably, the promoter is cell-type specific, preferably neurons specific.

Preferably, the promoter is the human synapsin-1 gene promoter.

In a particular embodiment, guide RNAs are targeting the deletion of nucleotides 70-132 of SEQ ID No: 1.

In another particular embodiment, guide RNAs are targeting the deletion of nucleotides 142-539 of SEQ ID No: 1.

In yet another particular embodiment, guide RNAs are targeting the deletion of nucleotides 70-132 and 142-539 of SEQ ID No: 1.

In still another particular embodiment, guide RNAs are targeting the deletion of nucleotides 4-539 of SEQ ID No: 1.

The invention also concerns means for targeted recombination of the human Dgkk gene of the invention for their use as a drug. Preferably, the invention concerns an expression vector comprising a promoter operably linked to the gene coding for the Crispr/Cas9 enzyme and the genes coding for guide RNAs of the invention, for their use as a drug, preferably in the treatment of fragile X syndrome in a subject in need thereof.

The invention also concerns a pharmaceutical composition comprising means for targeted recombination of the human Dgkk gene. Preferably, the inventions concerns a pharmaceutical composition comprising an expression vector comprising a promoter operably linked to the gene coding for the Crispr/Cas9 enzyme and the genes coding for guide RNAs of the invention, preferably in the treatment of fragile X syndrome in a subject in need thereof. Preferably the subject is a human.

The invention also concerns a method of treatment of fragile X syndrome in a subject in need thereof comprising the administration of an effective amount of an expression vector comprising a promoter operably linked to the gene coding for the Crispr/Cas9 enzyme and the genes coding for guide RNAs of the invention, or of a pharmaceutical composition according to the invention to the subject. Preferably the subject is a human.

The invention also concerns the use of an expression vector comprising a promoter operably linked to the gene coding for the Crispr/Cas9 enzyme and the genes coding for guide RNAs of the invention in the manufacture of a drug for the treatment of fragile X syndrome in a subject in need thereof. Preferably the subject is a human.

All the references cited in this application, including scientific articles and summaries, published patent applications, granted patents or any other reference, are entirely incorporated herein by reference, which includes all the results, tables, figures and texts of theses references.

Although having different meanings, the terms "comprising", "having", "consisting in" and "containing" can be replaced one for the other in the entire application.

Further aspects and advantages of the present invention will be described in the following examples, which should be regarded as illustrative and not limiting.

EXAMPLES

Example 1: Identification of the Regions Involved in the Control of Dgkk Expression by FMRP in Cos-1 Cells Material and Methods
Cell Culture:
COS cells (ATCC® CRL-1650™) were grown in DMEM supplemented with 10% fetal calf serum, 1 g/l glucose in the presence of antibiotics at 37° C. in 5% CO2. The day before transfection, 4×10⁴ cells were plated into 24-well format plates in 500 µl of antibiotic-free medium.

Plasmid Constructions:
Mouse Dgkκ was subcloned from clone IMAGE IRAVp968H03163D. The missing Dgkκ 3'UTR region was cloned by PCR from mouse genomic DNA with primers GCAGCTAGCTCCTTGAAAGCTGGAAGGAGA (SEQ ID No: 2) and AATAGAATGCGGCCGCCAGCTT-CAACAGCACTTGTAG (SEQ ID No: 3) and introduced at XbaI and NotI sites of the pYX-Dgkκ vector to give pYX-DgkκFull. Plasmid pCI-Dgkκ-FL (cf. FIG. 1, Table 1 above and SEQ ID No: 8) was obtained by PCR subcloning using pCI-DgkκFull as template (obtained by subcloning Dgkk into pCI vector GenBank U47119) with addition of the HA sequence before the STOP codon using the primers sense (TTCTCAACTATACCCATACGATGTTCCAGAT-TACGCTTAGTCCTTGAAAGCTGGAAGG, SEQ ID No: 4) and antisense (TCAAGGACTAAGCGTAATCTGGAA-CATCGTATGGGTATAGTTGAGAACTT-GAAGGTGTTG, SEQ ID No: 5).

Plasmid Δ5'reg-Dgkk (cf. FIG. 1) was obtained by subcloning the pYX-mDgkk into pEGF-N1 (U55762) and completed by enzymatic digestion of pCi-mDgkk-3'UTR and directed mutagenesis so as to insert tag HA and delete the 5' region.

Plasmid 5'reg-Dgkk (cf. FIG. 1) was obtained by inserting the 5' region fragment previously cloned into a pEGFP-C1 (U55763) vector and completed by directed mutagenesis so as to insert tag HA.

Δ5'UTR-5'reg-Dgkk, ΔPro-5'reg-Dgkk, ΔEPAPE-5'regDgkk, ΔEPAPE I-5'reg-Dgkk, and ΔEPAPE II-5'reg-Dgkk plasmids were obtained by direct mutagenesis of the pEGF-C1 5'reg plasmid, so has to remove the desired sequences (cf. FIG. 1).

TABLE 1

Positions of the main relevant domains of the Dgkκ-FL plasmid constructions
(numbering starts with the 5'UTR of the Dgkk gene)

| | Dgkk gene | | | | | | |
|---|---|---|---|---|---|---|---|
| | 5' region of the Dgkk gene | | | | Rest of | | |
| | 5'UTR | Beginning of the 5' region | Pro Rich Region | EPAPE repeated region | the Dgkk gene | Tag HA | 3'UTR |
| Plasmid Dgkκ-FL | 1-158 | 159-230 | 231-350 | 351-857* | 858-4208 | 4209-4235 | 4239-8085 |

*in the ΔEPAPE II-5'reg-Dgkk construction, the last five repetitions (on a total of ten) of the EPAPE motif have been deleted corresponding to the 531-857 sequence in the Dgkk-FL Plasmid Transfections and Western Blot Analyses:
Transfections of sh-RNAs were performed in triplicate with Lipofectamine 2000 (Invitrogen, Carlsbad, Calif.) on 60 000 cells as directed by the manufacturer with 20 pmol of siRNA (Control or On Target plus Smart Pool mouse FMR1, Thermo) in a final volume of 600 µl. Twenty-four hours later, 0.6 µg of a plasmid construction and 20 pmol of shRNA were co-transfected as above. Fourty-eight hours later, cells washed twice in PBS were lysed directly in the loading buffer (100 mM Tris-HCl, pH 6.8, 4% SDS, 30% glycerol, 1.4 M ß-mercaptoethanol, and bromophenol blue) for 3 min at 95° C. Proteins were analyzed on a 10% SDS-polyacrylamide gel and immunoblotted onto PVDF (Millipore) in Tris-glycine-SDS/20% ethanol buffer for 1 h at 200 mA. Membranes were incubated overnight at 4° C. with mouse anti-FMRP 1C3 1:10000, mouse anti-HA 1:1000 or mouse anti-GAPDH 1:10000 and incubated at room temperature with peroxidase-conjugated goat anti-mouse antibodies (1/5000). Immunoreactive bands were visualized with the SuperSignal West Pico Chemiluminescent Substrate (Pierce, Rockford, Ill.).

Results

The inventors have investigated the impact of FMRP on Dgkk expression in Cos-1 cells. Cos-1 cells were transfected with plasmids expressing either a full length Dgkk construct (Dgkk-FL, cf. FIG. 1), a Dgkk construct lacking its 5' coding region and its 5'-UTR (Δ5'reg-Dgkk, cf. FIG. 1) or a control plasmid. Both Dgkk constructs comprise a HA tag, allowing their detection with a specific antibody. Prior to plasmid transfection, Cos-1 cells were treated with siRNAs targeting Fmr1, or by a control siRNA.

Figure 2:
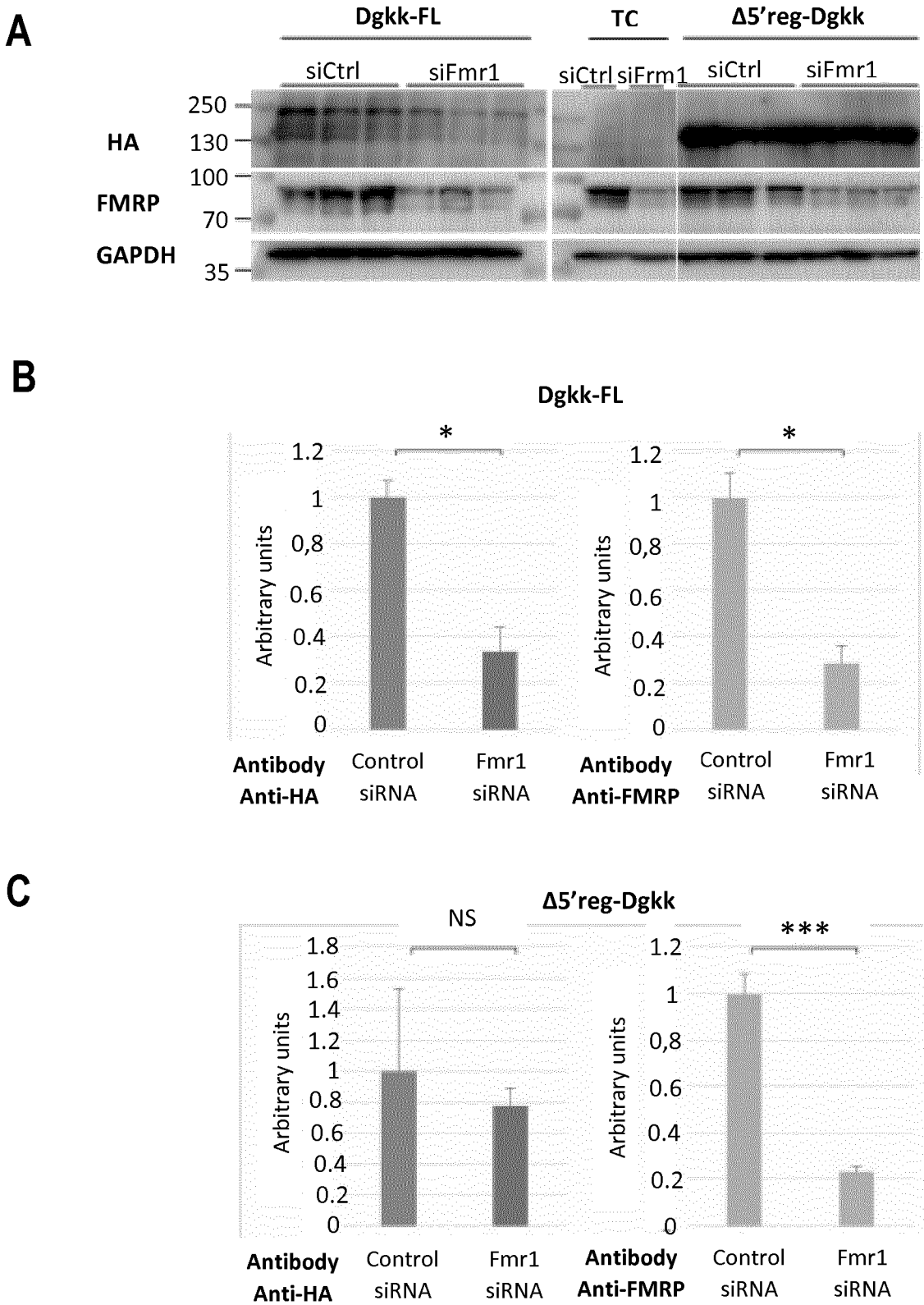
FIG. 2: Impact of FMRP on the expression of Dgkk in Cos-1 cells. A: Representative western-blot of the analysis of Cos-1 cells transfected with siRNA control (siCtlr) or siRNA against Fmr1 (siFmr1) 24 hours prior transfection with plasmids bearing the indicated Dgkk constructs (Dgkk-FL or Δ5'reg-Dgkk) or a Transfection Control (TC). The antibodies used are indicated: anti-HA antibody (HA), anti-FMRP antibody (FMRP) and anti-GAPDH antibody (GAPDH). B: Densitograms of the western blot for the constructions presented in A. The abscise represents arbitrary units of the signal of indicated protein (HA or FMRP) normalized to GAPDH set to 100 for siCtrl condition. * $p<0.001$,  $p<0.01$, * $p<0.1$, NS: Not significant, p value is calculated with the Student test, n=6.

Western-blot results with anti-FMRP antibodies show that siRNA targeting Fmr1 are efficient to reduce the expression of FMRP when compared to the control siRNA condition (cf. FIG. 2A). The expression of FMRP is reduced of about 70% (cf. FIG. 2B or 2C).

When FMRP expression is reduced, the expression level of Dgkk-FL is also reduced of about 70% in comparison to control conditions (cf. FIGS. 2A and 2B, with HA antibody). These results demonstrate that FMRP positively controls the expression of Dgkk.

On the opposite, the expression of the Δ5'reg-Dgkk construct is unaffected by the reduction of FMRP expression (cf. FIGS. 2A and 2C) demonstrating that Δ5'reg-Dgkk expression is not controlled by FMRP. These results underline that the Δ5' region, which comprise the 5' coding region and the 5'UTR of Dgkk, is of critical importance for the control of Dgkk expression by FMRP. Thus, the Δ5'reg-Dgkk construct, on the contrary to the full length Dgkk gene, can be expressed in cells lacking FMRP.

Figure 3:
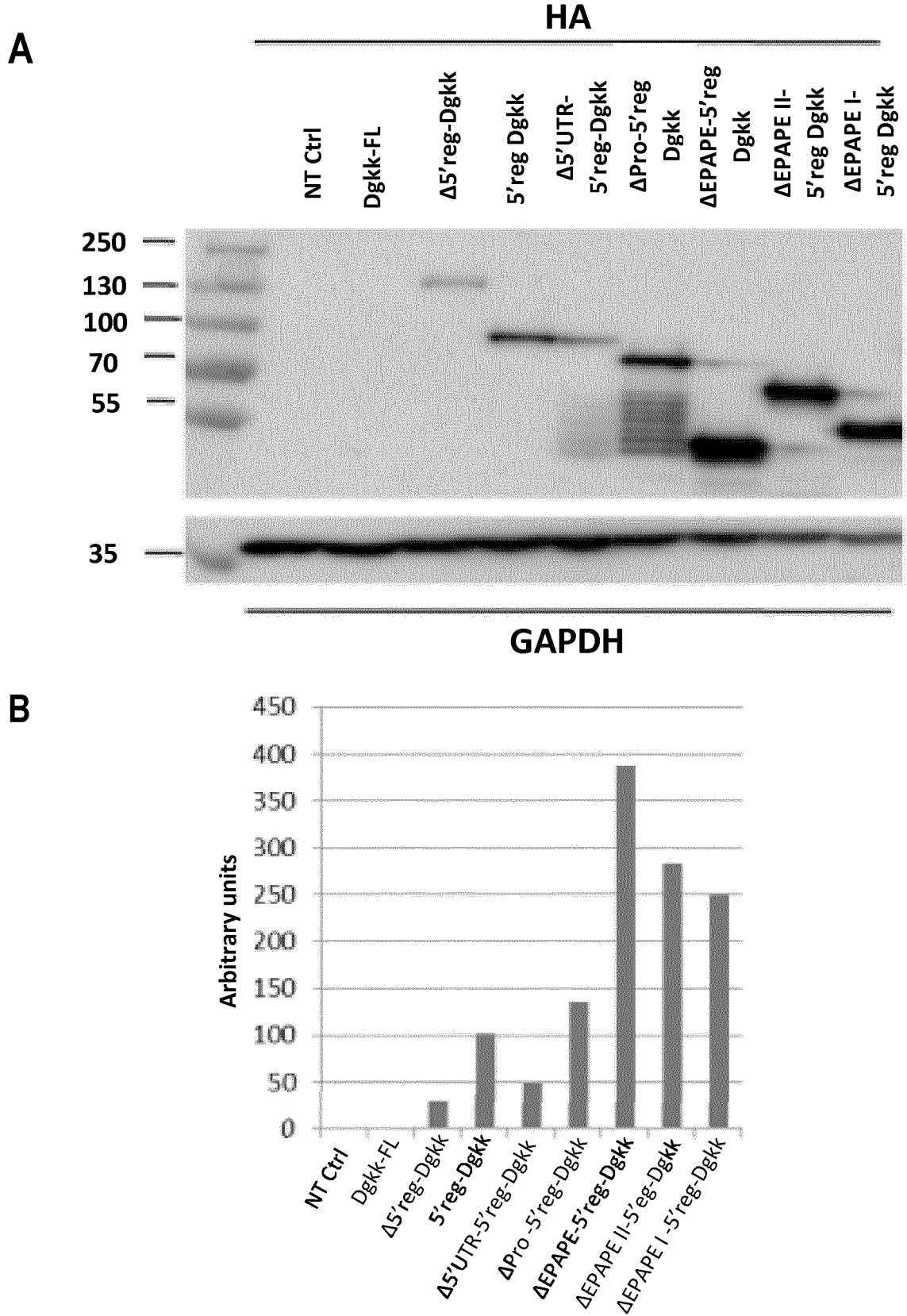
FIG. 3: Comparison of the expression of the different Dgkk constructions in Cos-1 cells. A: Representative western-blot of the analysis of Cos-1 cells either not transfected with a Dgkk construction (NT) or transfected with plasmids bearing the indicated Dgkk constructs. The antibodies used are indicated: anti-HA antibody (HA) and anti-GAPDH antibody (GAPDH). B: Densitograms of the western blot for the constructions presented in A. The abscissa represents arbitrary units of the signal of HA protein normalized to GAPDH.

Moreover, comparison of the intensity of the HA labelling between Δ5'reg-Dgkk and Dgkk-FL seems to indicate that, independently of FMRP control, the basal level of expression of Δ5'reg-Dgkk might be superior to the basal expression level of Dgkk-FL. In the experiment of FIG. 3, Cos-1 cells were transfected by different Dgkk constructions, including Dgkk-FL and Δ5'reg-Dgkk, and their expression was then analyzed by western-blot on the same gel. A significate difference of expression was found between the Dgkk-FL and the Δ5'reg-Dgkk constructs, confirming that the 5' region of Dgkk exerts a repressive action on the expression level of Dgkk.

Thus, suppressing the 5' region of Dgkk suppresses the positive control exerted by FMRP on Dgkk expression and enhances the expression of Dgkk.

In a second series of experiments, the inventors aimed to determine which part of the 5' region of Dgkk is important in the control of Dgkk expression by FMRP. To achieve this goal, the inventors made different constructs which all comprised a GFP and a HA tag for their detection (cf. FIG. 1). The first construct, 5'reg-Dgkk, comprises the sequence that was removed in the Δ5'reg-Dgkk construct: the 5' coding region of Dgkk and the 5'UTR of Dgkk. Then, in each other construct, a part of the 5'reg-Dgkk sequence was removed: the 5'UTR in the Δ5'UTR-5'reg-Dgkk construct, the Proline Rich Region in the ΔPro-5'reg-Dgkk construct, the EPAPE repeated region and the rest of 5'reg-Dgkk in the ΔEPAPE-5'reg-Dgkk construct, the EPAPE repeated region in the ΔEPAPE I-5'reg-Dgkk construct, and the second half of the EPAPE repeated region in the ΔEPAPE II-5'reg-Dgkk construct. Then, as previously described, Cos-1 cells were transfected by these constructs in the presence or absence of Fmr1 siRNA and the expression of the constructs was analyzed by western-blot.

Figure 4:
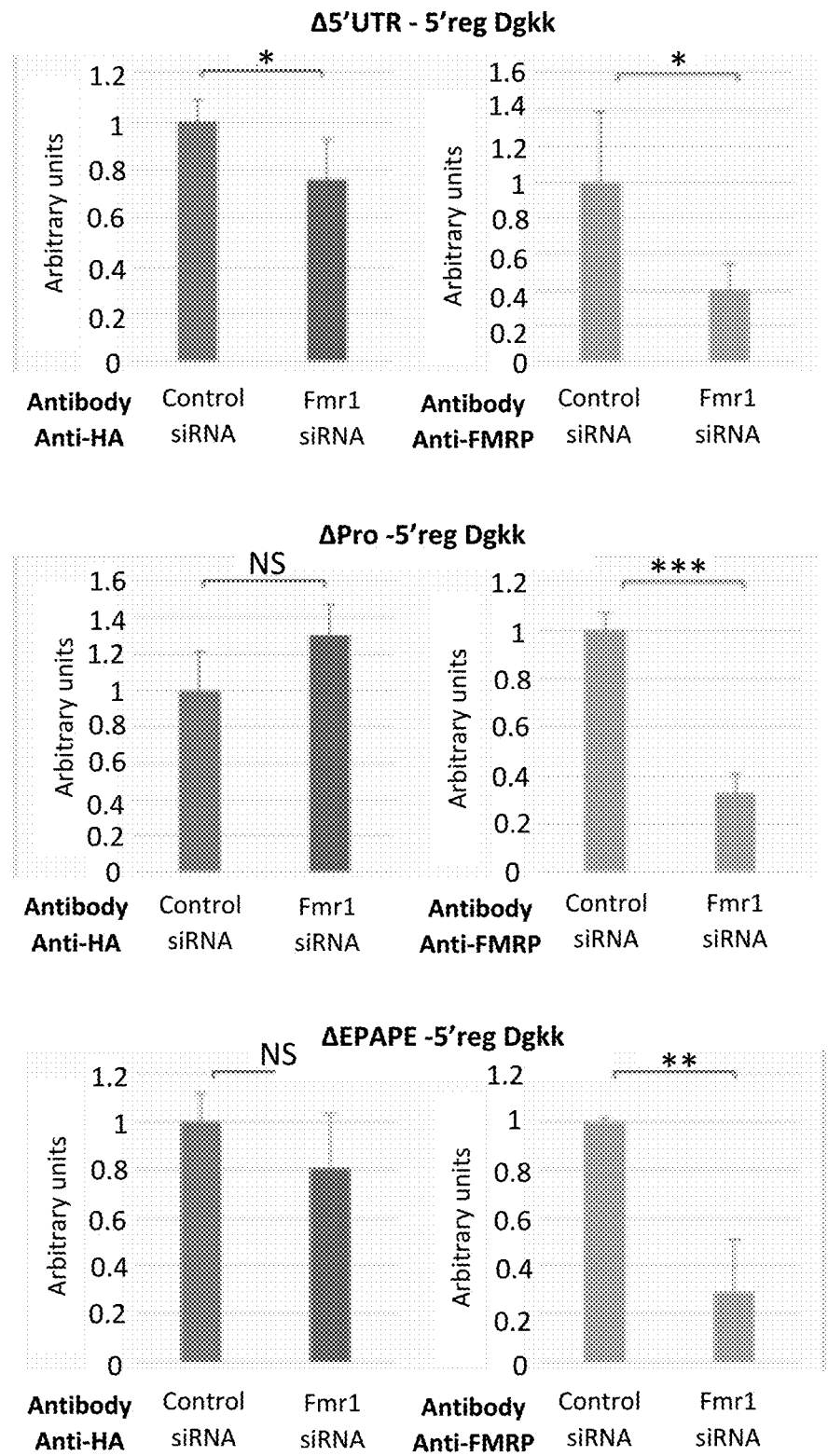
FIG. 4: Impact of the 5' region of Dgkk on the control of its expression by FMRP. A: Representative western-blot of the analysis of Cos-1 cells either not transfected with a Dgkk construction (NT) or transfected with plasmids bearing the indicated Dgkk constructs (indicated on the left). 24 hours prior transfection with the constructs, cells were transfected with siRNA control (siCtlr) or with siRNA against Fmr1 (siFmr1). The antibodies used are indicated: anti-HA antibody (HA), anti-FMRP antibody (FMRP) and anti-GAPDH antibody (GAPDH). B: Densitograms of the western blot for the constructions presented in A. The abscissa represents arbitrary units of the signal of indicated protein (HA or FMRP) normalized to GAPDH set to 100 for siCtrl condition. * $p<0.001$,  $p<0.01$, * $p<0.1$, NS: Not significant; p value is calculated with the Student test, n=6.
Figure 4:
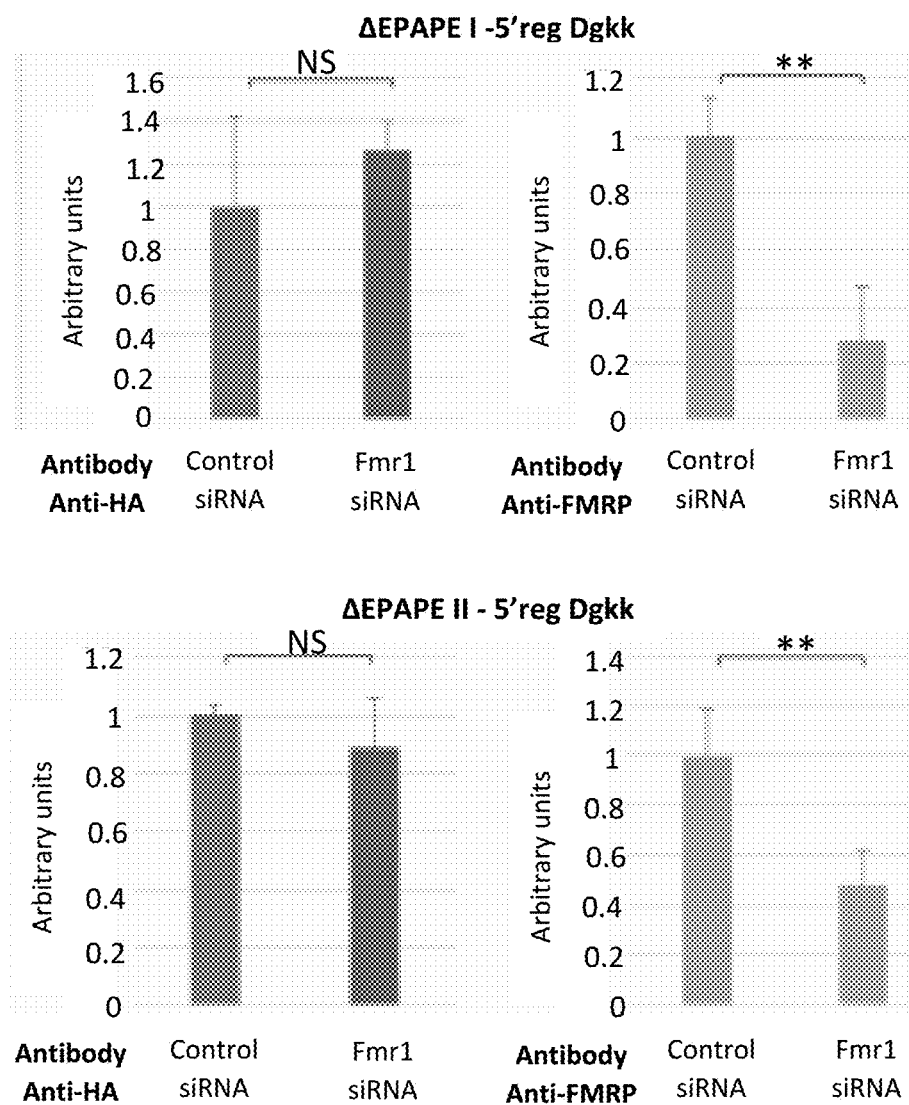

In the experiments with the 5'reg-Dgkk construct, the FMRP expression level was reduced of about 80% in cells transfected with Fmr1 siRNA in comparison to the control condition (FIGS. 4 A and B, first graphic). The expression level of 5'reg-Dgkk construct was also reduced of about 45% when FMRP expression level was reduced. These results demonstrate that the 5' region of Dgkk is sufficient to allow a positive control of the expression by FMRP.

In the experiments with the Δ5'UTR-5'reg-Dgkk construct, the FMRP expression level was reduced of about 60% in cells transfected with siRNA Fmr1 in comparison to the control condition (FIGS. 4 A and B, second graphic). The expression level of the Δ5'UTR-5'reg-Dgkk construct was reduced of about 25% when FMRP expression level was reduced. These results indicate that a control of the expression by FMRP is maintained in the absence of the 5'UTR in the 5' region of Dgkk. Thus, the 5'UTR doesn't seem of prime importance in the control of the expression of Dgkk by FMRP. Moreover, the apparent diminution of the control of the expression by FMRP from 50% to 30% in this experiment in comparison to the precedent, might be a consequence of the lower extinction of FMRP (50% instead of 80% in the precedent experiment).

In the experiment with the ΔPro-5'reg-Dgkk construct, the FMRP expression level was reduced of about 80% in cells transfected with siRNA Fmr1 in comparison to the control condition (FIGS. 4 A and B, third graphic). The expression level of the ΔPro-5'reg-Dgkk construct was unaffected by the reduction of the FMRP expression level. These results demonstrate that FMRP can't control the expression of the 5' region of Dgkk when the Proline Rich Region is removed from its sequence, demonstrating that the Proline Rich Region is of critical importance in the control of the expression of Dgkk by FMRP.

In the experiment with the ΔEPAPE-5'reg-Dgkk construct, the FMRP expression level was reduced of about 70% in cells transfected with siRNA Fmr1 in comparison to the control condition (FIGS. 4 A and B, fourth graphic). The expression level of the ΔEPAPE-5'reg-Dgkk construct was unaffected by the reduction of the FMRP expression level. These results demonstrate that FMRP can't control the expression of the 5' region of Dgkk when the EPAPE repeated Region is removed from its sequence, demonstrating that the EPAPE repeated Region is of critical importance in the control of the expression of Dgkk by FMRP.

In the experiment with the ΔEPAPE I-5'reg-Dgkk construct or with the ΔEPAPE II-5'reg-Dgkk construct, the FMRP expression level was reduced of about 60% in cells transfected with Fmr1 in comparison to the control condition (FIGS. 4 A and B, fifth and sixth graphics). The expression level of the ΔEPAP I-5'reg-Dgkk construct and ΔEPAPE II-5'reg-Dgkk were unaffected by the reduction of the FMRP expression level. These results demonstrate that FMRP cannot control the expression of the 5' region of Dgkk when totality or half of the EPAPE repeated Region are removed from its sequence, demonstrating that an incomplete EPAPE repeated Region is not enough to allow a control of the expression of Dgkk by FMRP.

Moreover, the comparison of the expression of the constructs 5'reg-Dgkk, Δ5'UTR-5'reg-Dgkk, ΔPro-5'reg-Dgkk, ΔEPAPE-5'reg-Dgkk, ΔEPAPE I-5'reg-Dgkk, and ΔEPAPE II-5'reg-Dgkk on the same gel shows that the expression level of the ΔPro-5'reg-Dgkk construct and especially the expression level of the ΔEPAPE-5'reg-Dgkk, ΔEPAPE I-5'reg-Dgkk, and ΔEPAPE II-5'reg-Dgkk constructs are higher than the expression level of the 5'reg-Dgkk, confirming that the Proline Rich Region and the EPAPE repeated Region exert a repressive action on the expression of Dgkk.

Altogether, these results demonstrate the importance of the Proline Rich Region and of the EPAPE repeated Region of Dgkk in the positive control of the expression of Dgkk by FMRP. The suppression of the 5' coding region of Dgkk, and in particular of the Proline Rich Region and/or of the EPAPE repeated Region, is sufficient to abolish the control of the expression of Dgkk by FMRP, such a modified Dgkk gene can thus be expressed in cells independently of FMRP expression level.

Example 2: Dendritic Spine Alterations and Rescue with Δ5'-DgkK Expression Modulation Material and Methods
AAV Vectors Construction:
A short hairpin RNA designed to target Dgkk (shRNA Dgkk, 5'-GGAATGCACTACTGGTATTCC, SEQ ID No: 6) and the selected shRNA-scramble sequence (5'-GCGCTTAGCTGTAGGATTC, SEQ ID No: 7) that has no match in silico in the mouse genome, were cloned under the control of the mU6 promoter into a pAAV-MCS derived plasmid expressing enhanced green fluorescent protein (EGFP) under the control of a CMV promoter. Overexpression of Dgkk was achieved by cloning HA-tagged Δ5'reg-Dgkk under the control of the human Synapsin-1 gene promoter replacing EGFP in the control plasmid pENN.AAV.hSynapsin1.EGFP.RBG (provided by the Penn Vector Core at University of Pennsylvania). Recombinant adeno-associated virus serotype 9 (AAV9) co-expressing EGFP and shRNA (AAV9-EGFP-shRNA-Dgkk and control AAV9-EGFP-shRNA-scramble) as well as AAV9 expressing HA-Dgkk or EGFP (AAV9-hSynapsin1-HA-Dgkk and control AAV9-hSynapsin1-EGFP) were generated. AAV production was carried out using the AAV Helper-Free system (Agilent Technologies) with some modifications. AAV9 vectors were generated by triple transfection of 293T/17 cell line using either pAAV-EGFP-shRNA-Dgkk or pAAV-EGFP-shRNA-scramble, pAAV-hSynapsin1-HA-Δ5'reg-Dgkk or pENN.AAV.hSynapsin1.EGFP.RBG together with pAAV2/9 (Penn Vector Core) containing cap genes of AAV serotype 9 and pHelper. Two days after transfection, cells were collected, lysed by three freeze/thaw cycles in dry ice-ethanol and 37° C. baths, further treated with 100 U/ml Benzonase (Novagen) for 30 min at 37° C. and clarified by centrifugation. Viral vectors were purified by iodixanol (Optiprep™, Axis Shield) gradient ultracentrifugation followed by dialysis and concentration against PBS containing 0.5 mM MgCl2 using centrifugal filters (Amicon Ultra-15 100 K). Viral particles were quantified by real time PCR using a linearized standard plasmid pAAV-EGFP. To achieve comparable working concentrations, viruses were diluted to a final concentration of $5 \times 10^{12}$ viral genomes per ml (vg/ml) and stored at −80° C. until use.

Slice Cultures Transfection and Imaging:
Hippocampal organotypic slice cultures (400 µm thick) were prepared from postnatal 5-6 day old C57BL/6 Fmr1+/y or its Fmr1−/y littermate mice using a protocol approved by the Geneva veterinary office and maintained under culture conditions as described (De Roo M et al, 2008, Cereb Cortex, 18(1):151-161). Transfection was carried out at DIV7 with a biolistic method (Helios Gene Gun, Bio-Rad) using gold beads coated with mRFP and either pAAV-EGFP-shRNA-Dgkk, pAAV-EGFP-shRNA-scramble, pAAV-hSynapsin1-EGFP or pAAV-hSynapsin1-HA-Δ5'reg-Dgkk. Repetitive confocal imaging was performed as previously described (De Roo M et al, 2008, Cereb Cortex, 18(1):151-161). Briefly, dendritic segments of CA1 transfected neurons (30-40 µm in length) were imaged from DIV12 to DIV15 (at 0, 5, 24, 48 and 72 hours) using an Olympus Fluoview 300 system and analysis of the Z-stacked images so obtained was performed using Osirix software.

Figure 5:
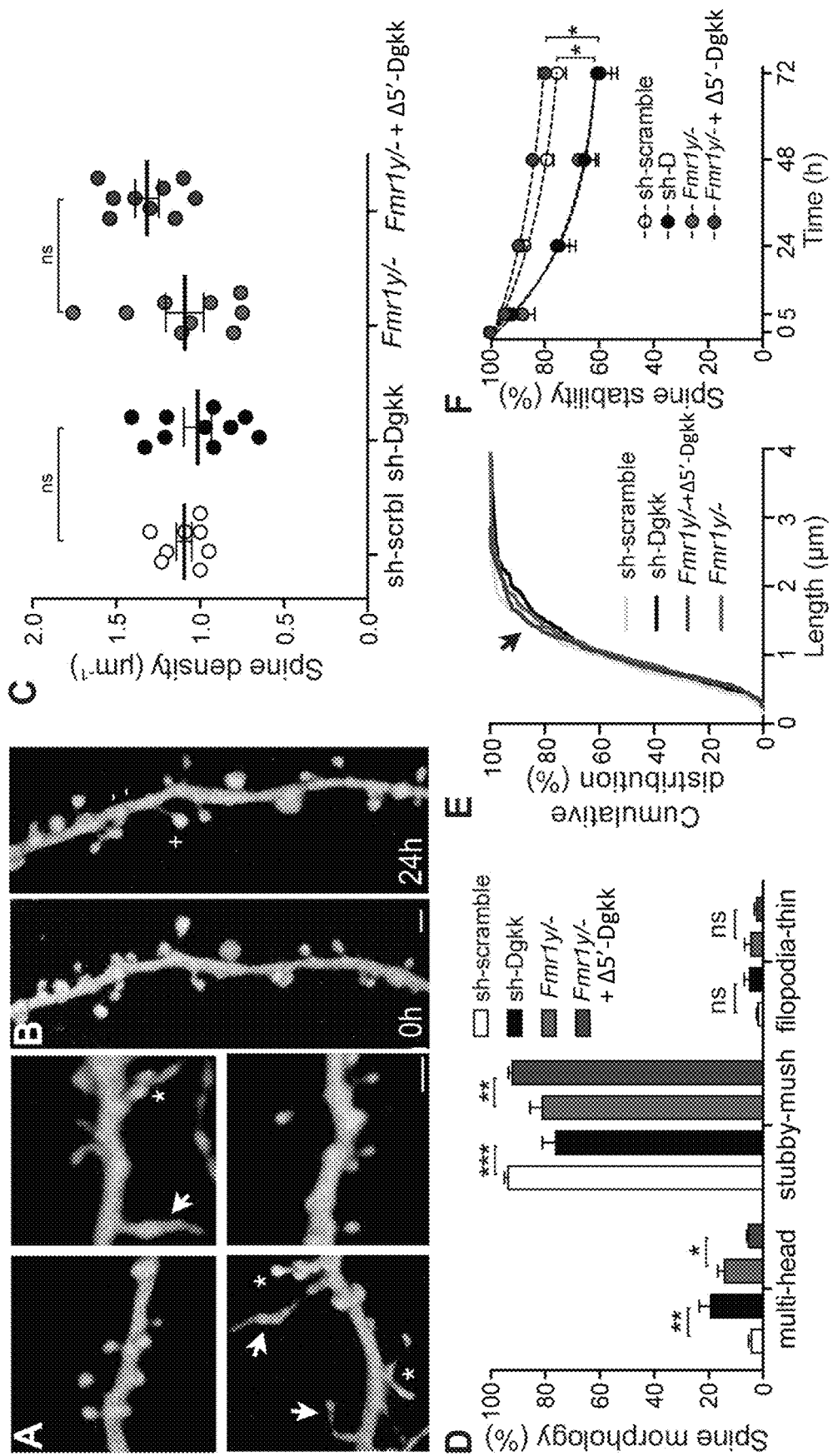
FIG. 5: Dendritic spine alterations and rescue with Δ5'-Dgkk expression modulation. A: Illustration of the changes in spine morphology induced by expression of shRNA-scramble (top left), shRNA-Dgkk (bottom left), Fmr1−/y (top right), Fmr1−/y+ Δ5'-Dgkk (bottom right), in CA1 pyramidal neurons transfected with pAAV-EGFP-shRNA-scramble, pAAV-EGFP-shRNA-Dgkk, pAAV-EGFP, pAAV-Δ5'-Dgkk, respectively. Note the presence of multiheaded spines (stars) as well as very long thin spines (arrows; bar: 2 μm). B: Spine changes (new spines, +, and lost spines, −) occurring in shRNA-scramble expressing pyramidal neurons (bar: 2 μm). C: Absence of changes in spine density under the four conditions. D: Increase in multi-head spines and decrease in mushroom spines in shRNA-Dgkk (sh-Dgkk) (n=10) versus shRNA-scramble (sh-scrbl) transfected cells (n=8) and in Fmr1−/y (FMRKO) (n=8) versus Fmr1−/y+Δ5'-Dgkk (FMRKO+Δ5'-DGKK) transfected cells (n=8; *: $p<0.05$; : $p<0.01$; *: $p<0.001$, 2way ANOVA with Bonferroni post-test). E: Distribution of spine lengths in shRNA-Dgkk (n=342 spines), shRNA-scramble (n=297 spines), Fmr1−/y (n=359 spines), Fmr1−/y+Δ5'-Dgkk (n=377 spines) transfected cells (p=0.13, Kolgomorov-Smirnov test). F: Decrease in spine stability over time (*: $p<0.05$, 2way ANOVA with Bonferroni post-test), G: Dendritic spines morphology and dynamics alterations induced by expression of shRNA-Dgkk (right) or a shRNA-scramble (left) in CA1 pyramidal neurons. Time (h) is indicated. The pictures correspond to repetitive confocal images taken at the indicated times of mouse hippocampal organotypic cultures transfected by biolistic method (materials and methods) with plasmid vectors expressing shRNA-Dgkk or shRNA-scramble. H: Increase in new spine formation per 24 h in shRNA-Dgkk (n=10) versus shRNA-scramble (n=8) transfected cells (**: $p<0.01$, unpaired t-test). I: Increase in lost spines per 24 h (*: $p<0.05$, unpaired t-test).
Figure 5:
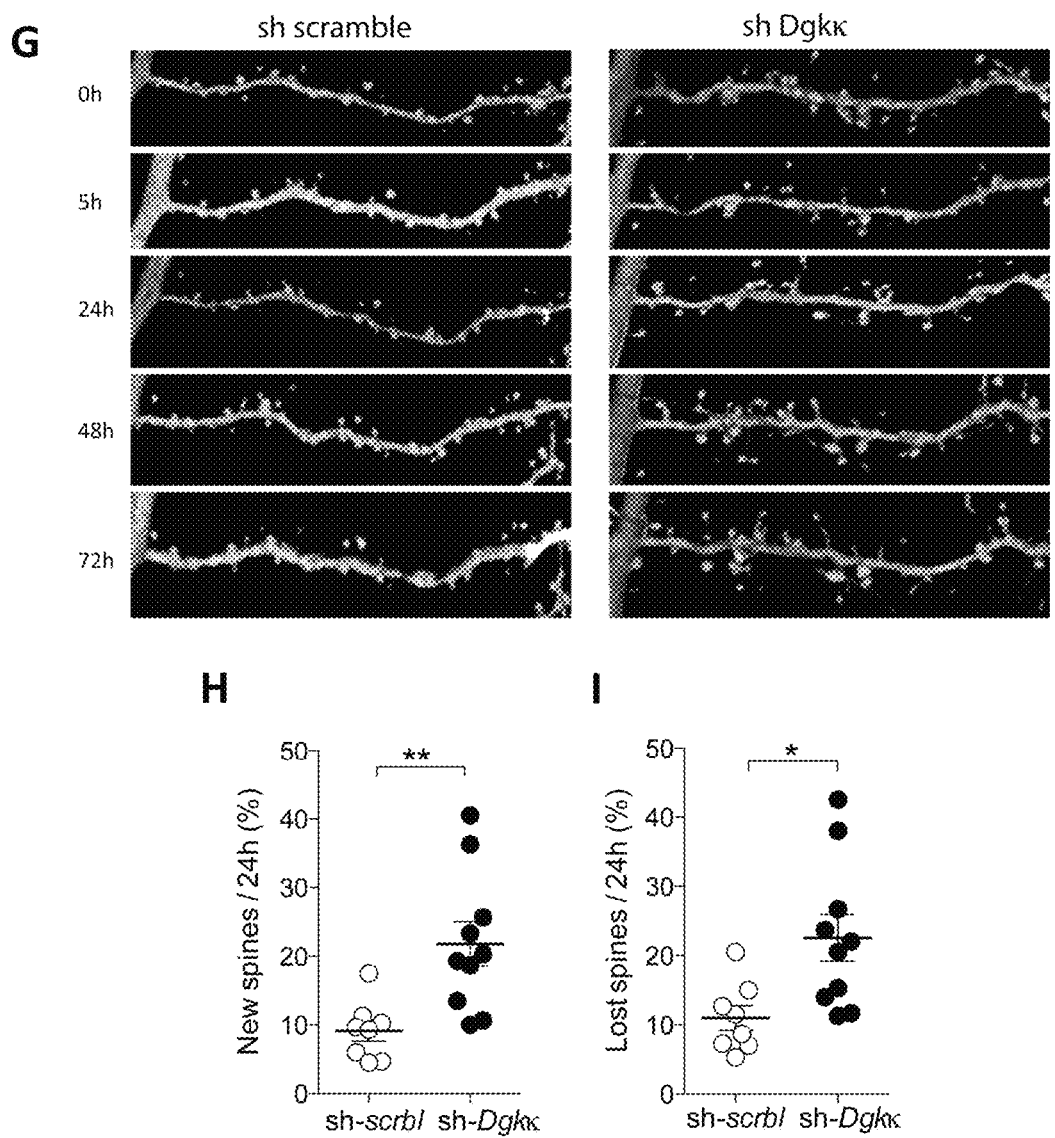

Results
The inventors examined the impact of Dgkk loss of function on dendritic spines morphology and dynamics. Dgkk silencing in CA1 region of mouse hippocampus organotypic slices causes a strong increase of abnormally long and multi-headed spines and a marked decrease of the proportion of mature spines (cf. FIG. 5A-D), while spine density remains unchanged (cf. FIG. 5C). Additionally, there is a significant increase of spine turnover, as indicated by the increased rate of spine formation and elimination, associated with spine instability (cf. FIG. 5 G-I). These data indicate that Dgkk is necessary for spine maturation and maintenance and that its loss leads to structural defects similar to those previously observed in the Fmr1−/y mice (Comery T A et al, 1997, Proc Natl Acad Sci USA, 94(10):5401-5404; He C X & Portera-Cailliau C, 2013, Neuroscience, 251:120-128). To establish a functional link between Dgkk and FMRP, the inventors tested whether the over-expression of Δ5'reg-Dgkk within Fmr1−/y neurons could rescue the dendritic spine phenotype. Remarkably, Fmr1−/y neurons transduced by AAV9 expressing Δ5'reg-Dgkk have their spine defects corrected (cf. FIG. 5A-F Fmr1−/y+Δ5'reg-Dgkk), indicating that Δ5'reg-Dgkk overexpression is able to compensate for the lack of FMRP.

Example 3: Transduction of AAV Δ5'Reg-DgkK In Vitro and In Vivo, and Impact on Fmr1-KO Mouse Behavior Material and Methods
AAV Vectors Construction:
Recombinant adeno-associated virus serotype 9 (AAV9) and RH10 (AAV10) expressing HA-tagged Δ5'reg-Dgkk under the control of the human Synapsin-1 gene promoter (AAV9-Δ5'reg-Dgkk and AAV10-45'reg-Dgkk) were prepared as described in example 2.

Primary Cortical Neuron Cultures:
Cortices from C57BL/6J Fmr1+/y or Fmr1−/y mouse embryos [embryonic day (E17.5)] were dissected in 1×PBS, 2.56 mg/mL D-glucose, 3 mg/mL BSA, and 1.16 mM MgSO4; incubated for 20 min with 0.25 mg/mL trypsin and 0.08 mg/mL DNase I; and mechanically dissociated after supplementation of medium with 0.5 mg/mL trypsin soybean inhibitor, 0.08 mg of DNase I and 1.5 mM MgSO4. The cells were plated on poly-L-lysine hydrobromide-coated six-well culture plates for 8 d in Neurobasal Medium (GIBCO) supplemented with B27, penicillin/streptomycin, and 0.5 µM L-glutamine.

Stereotaxic Surgery and AAV Injections

Mice (C57BL/6J) were deeply anesthetized with ketamine/xylazine (Virbac/Bayer, 100/10 mg/kg, 10 mL/kg, intraperitoneal) dissolved in sterile isotonic saline (NaCl 0.9%) and mounted onto a stereotaxic frame (Unimecanique). AAV9-Δ5'reg-Dgkk, AAV10-Δ5'reg-Dgkk or AAV9-EGFP ($5 \times 10^{12}$ viral genomes per mL) was injected bilaterally both in the striatum and in the hippocampus according to the mouse brain atlas coordinates. A volume of 1.5 µL of AAV vectors per site of injection was delivered bilaterally with a slow injection rate (0.1 μL/min) through a 30-gauge stainless steel cannula connected to an infusion pump. After each injection was completed, the injector was left in place for an additional 10 min to ensure optimal diffusion and minimize backflow while withdrawing the injector. Behavioral experiments were conducted 4 weeks after AAV injections to allow sufficient time for viral transduction and Dgkκ expression. Effective gene expression was assessed by qRT-PCR and by immunofluorescence.

Behavioral Experiments:

Behavioral testing was performed blind in a battery on AAV9-Δ5'reg-Dgkk, AAV10-Δ5'reg-Dgkk or AAV9-EGFP treated mice 4 wk after striatal injection. Direct social interaction and NOR were performed in four equal square arenas (50×50 cm) separated by 35-cm-high opaque gray Plexiglas walls over a white Plexiglas platform (View Point).

Direct Social Interaction:

On day 1, mice were placed in each arena for 15-min habituation. On day 2, a pair of animals (same condition, not cage mates) was introduced in each arena for 10 min. Total time spent in close contact (nose and paw contacts), number and duration of nose and paw (crawling over, mounting, stepping on, and pushing) contacts, and allogrooming, as well as number of following, rearing, and circling episodes, were scored on video recordings. We observed no aggressive behavior (attacks, bites, or tail rattling) between protagonists during this test.

Physical Condition:

Physical performance was assessed with a rotarod (Bioseb) accelerating from 4 to 40 rpm in 5 min. The rod was covered with insulation tubing for better grip, which external perimeter was 5 cm (40 lx). On day 1, mice were habituated to rotation on the rod at 4 rpm, until they were able to stay >180 s. From day 2 to 5, mice were tested for three daily trials (60-s intertrial). Each trial started by placing the mice on the rod and beginning rotation at constant 4-rpm speed for 60 s. Then the accelerating program was launched, and the trial ended for a particular mouse when they fell off the rod. Time on the rod was automatically recorded. Novel Object Recognition (NOR):

The NOR test was performed as described (Le Mercer et al. (2013) Neuropsychopharmacology 38(6):1050-1059). Briefly, on day 1, the animals were placed in an arena for 15-min habituation with two copies of an unfamiliar object. On day 2, the recognition test consisted of three trials of 10 min separated by two intertrial intervals of 5 min. On familiarization phase, the mice were presented with two copies of an unfamiliar object. On place phase, one of the two copies was displaced to a novel location in the arena. On object phase, the copy that had not been moved on previous trial was replaced by a novel object. Stimuli objects sized 1.5-3×2-3 cm. The identity of the objects and their spatial location were balanced between subjects. The number of visits and the time spent to explore each object were scored on video recordings. A percentage of discrimination was calculated for number of visits and time exploring the objects as following: exploration of displaced or novel object/total exploration ×100. The pattern of quadrant crossings was quoted on video recordings. Full explorations (FE; i.e., successive crossings of the four quadrants forming overlapping quadruple sets, e.g., ABCD), quadrant returns (QR; e.g., ABCB), and quadrant alternations (QA; e.g., ABAB) were scored, and the percentage of FE, QR, and QA was calculated as following: FE or QR or QA/(total crossings)×100.

Spontaneous Activity:

Measurement of spontaneous activity and food/water intake was assessed in automated cages (Imetronic, Pessac, France) for evaluation of biological rhythm and sleep abnormalities during 24 h periods. The cages were illuminated 12 hrs per day starting from 7 a.m. The rack was connected to an electronic interface to communicate with a computer for automatic data storing. Each mouse was introduced into an activity cage at 6 p.m. and left undisturbed for the subsequent 25 hrs. Locomotor activity was evaluated based on the number of breaks of the infrared captors. The first testing hour was analyzed separately in 10-min bins, in order to evaluate the locomotor response and habituation to a novel environment. The remaining 24 hrs were analyzed in 1 hr-blocks with the 12 hr-dark/light phase as a further within subject factor, in order to assess the circadian modulation of locomotor activity.

Statistical Analysis:

All data were analyzed by ANOVA with genetic background B6 and Fmr1 genotype (y/+ or y/-) as between-subject factors. Within-subject factors were included as needed. Post-hoc comparisons were performed using Fisher's LSD test. Data are presented as mean±SEM.

Results

Figure 6:
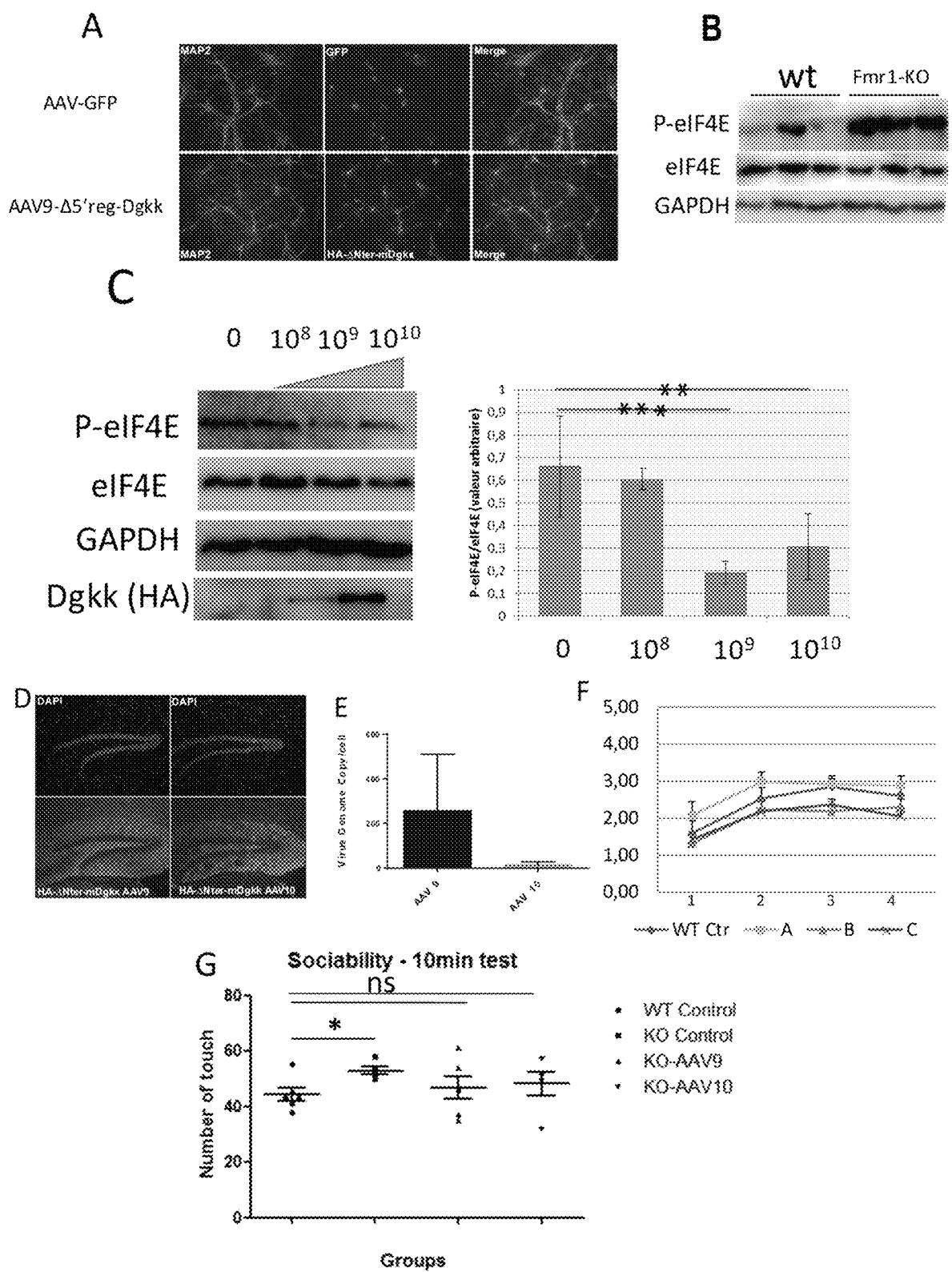
FIG. 6: Transduction of AAV Δ5ransductκ in vitro and in vivo, and impact on Fmr1-KO mouse behavior. A) Dissociated cortical neurons (14 days in vitro) are efficiently transduced with AAV9-Δ5'reg-Dgkk. Dgkk is visualized by immunolabeling using anti-HA primary antibody. AAV-GFP is shown as a transduction positive control. Map2 is a marker of neurons. B) Phosphorylation of initiation factor 4E (eIF4E) is increased in Fmr1−/y neurons. Western blot analysis performed on 10 μg protein extract of cortical neurons (14 DIV) with the indicated primary antibody. Three biological replicates are shown. C) Δ5'reg-Dgkk expression from AAV9 reduces eIF4E phosphorylation in Fmr1−/y neurons 7 days post-infection. Data correspond to western blot perform as in B. The titer of virus (genome copies) is indicated. The densitogram analysis of the western blot is presented on right. P value * <0.001,  ≤0.01, with student T test n=4. D) Immunofluorescent labelling of Δ5'reg-Dgkk with anti-HA antibody (green) on hippocampal regions of mice injected with indicated vectors. E) Quantification of virus genome copy/cell by qRT-PCR in hippocampus of mice treated as in D (AAV9 and AAV 10 correspond to AAV9-Δ5'reg-Dgkk and AAV10-Δ5'reg-Dgkk, respectively). F) Physical performance of treated mice was tested with accelerating rotarod test. Data correspond to latency to fall (min) over 4 days sessions (1-4), meance treated as in D (AAV9 and AAV 10 correspond to AAV9-erroups (T test). Wt Ctr, Fmr1 y/+ treated saline; A, Fmr1Y/− treated saline; B Fmr1Y/− treated AAV9-Δ5'reg-Dgkk; C, B Fmr1Y/− treated AAV9-Δ5'reg-Dgkk. G) Direct social interaction. Number of touch between 2 mice of same genotype is indicated (mean. Data coP≤0.05 T-test, n=10). Wt control, Fmr1 y/+ treated saline; KO control, Fmr1Y/− treated saline; KO-AAV9, Fmr1Y/− treated AAV9-Δ5'reg-Dgkk; KO-AAV10, Fmr1Y/− treated AAV9-Δ5'reg-Dgkk. H) Novel object recognition test. % sniffing time is indicated for novel object (NO) and familiar object (FO) on second day of testing. Data are means±SEM, *** P≤0.001 T-test, n=10. Name of groups as in G. I) Actimetry test. Data are means±SEM of light beam interruption over 24 h period, animal groups are labelled as in F, *P≤0.05 with T-test, n≥9, ns non significant. J) Detail of actimetry measurements. Data are means±SEM of light beam interruption as in I. P values for each time period are shown.
Figure 6:
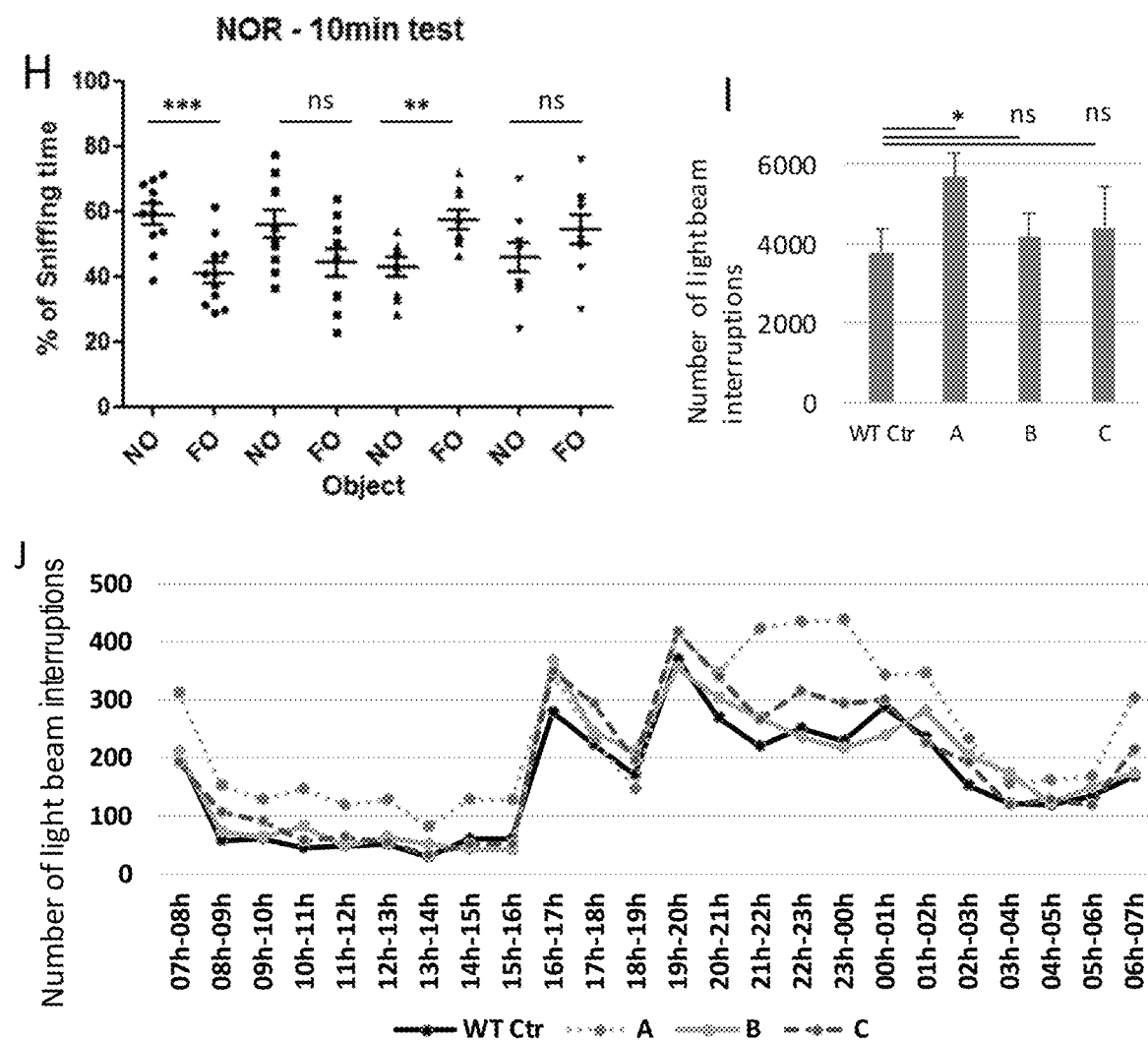

The inventors examined the impact of Δ5'reg-Dgkk expression from adeno-associated virus serotype 9 (AAV9) or rh10 (AAV10) in dissociated neuron cultures or in vivo in C57BL/6 Fmr1+/y or its Fmr1-/y littermate mice. Cortical neurons from C57BL/6 Fmr1+/y or its Fmr1-/y littermate mice are efficiently transduced (±100%) at 14 days in vitro and Δ5'reg-Dgkk transgene is well expressed as visualized with HA-tag (FIG. 6A). Phosphorylation of initiation factor 4E (eIF4E) has been shown previously to be increased in Fmr1-/y neurons and in patients (Gantois et al. *Nat Med.* 2017 June; 23(6):674-677, FIG. 6B) and eIF4E phosphorylation is proposed to result from the overactivation of the metabotropic glutamate receptor (mGluR) signaling in Fragile X condition. The inventors showed that expression of Δ5'reg-Dgkk expression from AAV9 (FIG. 6C) or AAV10 (data not shown) reduces eIF4E phosphorylation in Fmr1-/y neurons 7 days post-infection. These data indicate that AAV9-Δ5'reg-Dgkk or AAV10-Δ5'reg-Dgkk vectors have potential to correct abnormal eIF4E phosphorylation in Fmr1-/y neurons. The inventors examined next the ability of Δ5'reg-Dgkk expression from AAV9 or AAV10 to correct behaviors of Fmr1-/y mouse. C57BL/6J Fmr1+/y or Fmr1-/y mice received injections of AAVs (2×10E10 GC/injection site) both in striatal and in hippocampal regions at 4 weeks of age. 4 weeks after injection, the effective gene expression was assessed by qRT-PCR and by immunofluorescence (FIG. 6D, E). Expression of Δ5'reg-Dgkk expression from AAV9 or AAV10 had no impact on the physical conditions of mice independently of the genotype (Figure). Fmr1-/y mice have increased interaction time with stranger mice (reduced anxiety) compared to wild type Fmr1+/y (FIG. 6A). Δ5'reg-Dgkk expression from AAV9 or AAV10 correct this phenotype (FIG. 6A). Fmr1-/y mice have decreased memory in novel object recognition (NOR) test compared to wild type Fmr1+/y (Bhattacharya et al, 2012). While the Fmr1-/y mice lack the ability to discriminate new versus familiar object, the AAV9-Δ5'reg-Dgkk treated animal show a discrimination ability for the familiar versus novel object (FIG. 6H). These data suggest a partial efficiency of the treatment on the memory of animals. The targeting of the AAV to specific brain regions could explain a partial recovery. Fmr1-/y mice have increased activity throughout a 24 hour period (hyperactivity) compared to wild type Fmr1+/y (FIG. 6I). Δ5'reg-Dgkk expression from AAV9 or AAV10 correct this phenotype (FIG. 6I). Altogether these data suggest that Δ5'reg-Dgkk expression has the ability to ameliorate phenotypes of the Fmr1-/y mouse model of fragile X.

The invention claimed is:

1. A pharmaceutical composition comprising a nucleic acid encoding a human DGKk (Diacylglycerol Kinase kappa) protein that catalyzes the phosphorylation of diacylglycerol and lacks a functional Proline Rich Region and/or a functional EPAPE repeated Region, wherein the nucleic acid has the sequence of SEQ ID NO: 1 and comprises a deletion of a sequence selected from the group consisting of positions 70-132 of SEQ ID NO: 1, positions 142-539 of SEQ ID NO: 1, positions 70-132 and 142-539 of SEQ ID NO: 1, and positions 4-539 of SEQ ID NO: 1.

2. The pharmaceutical composition according to claim 1, wherein the pharmaceutical composition comprises an expression cassette comprising said nucleic acid and a promoter.

3. The pharmaceutical composition according to claim 2, wherein the promoter is a neuron specific promoter.

4. The pharmaceutical composition according to claim 1, wherein the pharmaceutical composition comprises an expression vector comprising said nucleic acid.

5. The pharmaceutical composition according to claim 4, wherein the expression vector is an adeno-associated virus.

6. The pharmaceutical composition according to claim 5, wherein the adeno-associated virus is AAVrh10.

7. A pharmaceutical composition comprising a nucleic acid encoding a human DGKk (Diacyclglycerol Kinase kappa) protein that catalyzes the phosphorylation of diacylglycerol and lacks a functional Proline Rich Region and/or a functional EPAPE repeated Region, wherein the nucleic acid has at least 85% identity with SEQ ID NO: 1 and further comprises a deletion of a sequence selected from the group consisting of positions 70-132 of SEQ ID NO:1, positions 142-539 of SEQ ID NO: 1, positions 70-132 and 142-539 of SEQ ID NO: 1, and positions 4-539 of SEQ ID NO: 1, and wherein said nucleic acid encodes a human DGKk protein comprising a Pleckstrin homology domain comprising amino acids 216 to 309 of SEQ ID NO: 9 and a catalytic domain comprising amino acids 487-622 of SEQ ID NO: 9.

8. The pharmaceutical composition according to claim 7, wherein the pharmaceutical composition comprises an expression cassette comprising said nucleic acid and a promoter.

9. The pharmaceutical composition according to claim 7, wherein the promoter is a neuron specific promoter.

10. The pharmaceutical composition according to claim 7, wherein the pharmaceutical composition comprises an expression vector comprising said nucleic acid.

11. The pharmaceutical composition according to claim 10, wherein the expression vector is an adeno-associated virus.

12. The pharmaceutical composition according to claim 11, wherein the adeno-associated virus is AAVrh10.

13. A method of treating fragile X syndrome in a patient comprising the administration of a pharmaceutical composition according to claim 7 to said patent.

* * * * *

UNITED STATES PATENT AND TRADEMARK OFFICE
CERTIFICATE OF CORRECTION

PATENT NO. : 11,597,936 B2
APPLICATION NO. : 16/336488
DATED : March 7, 2023
INVENTOR(S) : Hervé Moine and Ricardos Tabet It is certified that error appears in the above-identified patent and that said Letters Patent is hereby corrected as shown below:

In the Specification

Column 26,
Line 1, "pAAV-hSynapsin1-HA-45'reg-Dgkk." should read --pAAV-hSynapsin1-HA-Δ5'reg-Dgkk.--.
Line 43, "AAV10-45'reg-Dgkk)" should read --AAV10-Δ5'reg-Dgkk)--.

Column 27,
Line 43, "(Le Mercer" should read --(Le Merrer--.

Signed and Sealed this
Fifth Day of September, 2023

Katherine Kelly Vidal
*Director of the United States Patent and Trademark Office*